United States Patent
Brunken et al.

(10) Patent No.: US 6,693,169 B1
(45) Date of Patent: Feb. 17, 2004

(54) LAMININ 5, 13 AND 14 AND USES THEREOF

(75) Inventors: William J. Brunken, Canton, MA (US); Richard R. Libby, Hingham, MA (US); Dale D. Hunter, Canton, MA (US); Robert E. Burgeson, Marblehead, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/415,625

(22) Filed: Oct. 12, 1999

Related U.S. Application Data

(60) Provisional application No. 60/104,430, filed on Oct. 15, 1998, and provisional application No. 60/104,044, filed on Oct. 13, 1998.

(51) Int. Cl.[7] .............................................. C07K 14/78
(52) U.S. Cl. ...................................... 530/350; 530/362
(58) Field of Search .......................... 435/320.1, 252.3, 435/365.1; 514/8; 536/23.1; 530/350, 362

(56) References Cited

PUBLICATIONS

Iivanainen et al. The Journal of Biochemistry. vol. 274 (20):14107–14111, 1999.*
Ljubimov et al. (Laboratory Investigation (1995) 72(4):461–473.*
Aberdam et al. (1994) *Cell Adhes. Commun.*, 2:115–129.
Burgeson et al. (1994) *Matrix Biol.*, 14:209–211.
Miner et al. (1997) *J. Cell Biol.*, 137:685–701.
Hunter et al. (1992) *Neuron*, 8:399–413.
Hunter and Brunker (1997) *Mol. Cell Neurosci.*, 10:7–15.
Hunter et al. (1992) *J. Comp. Neurol.*, 323:238–251.
Dong et al. (1991) *Differentiation*, 48:157–172.
Morissette et al. (1995) *J. Neurosci.*, 15:8067–8082.
Libby et al. (1996) *Opthalmol. Vis. Sci.*, 37:1651–1661.
Hunter et al. (1989) *Nature*, 338:229–234.
Noakes et al. (1995) *Nature*, 374:258–262.
Libby et al. (1997) *J. Comp. Neurol.*, 389:355–367.
Sanes et al. (1983) *Cold Spring Harb. Symp. Quant. Biol.*, 48:667–678.
Sanes et al. (1996) *J. Cell Biol.*, 111:1685–1699.
Sugiyama et al. (1995) *Eur. J. Biochem.*, 228:120–128.
Toti et al. (1997) *Neuromusc. Disord.*, 7:21–25.
Utani et al. (1995) *Lab. Invest.*, 72:300–310.
Kallunki et al. (1992) *J. Cell Biol.*, 119:679–693.
Bunt–Milam et al. (1983) *J. Cell Biol.*, 97:703–712.
Libby et al. (1998) *IOVS Supplement*, 39:S57.
Cornbrooks et al. (1983) *PNAS USA*, 80:3850–3854.
Palm et al. (1983) *J. Cell Biol.*, 96:1218–1226.
Chiu et al. (1991) *Glia*, 4:11–24.
Xu et al. (1994) *Nat. Genetics*, 8:297–302.
Sunada et al. (1995) *Hum. Mol. Genet.*, 4:1055–1061.
Helbling et al. (1995) *Nat. Genet.*, 11:216–218.
Liesi et al. (1983) *J. Cell Biol.*, 96:920–924.
Liesi et al. (1989) *Exp. Neurol.*, 105:86–92.
Liesi et al. (1995) *J. Neurosci. Res.*, 40:199–206.
Sanes et al. (1989) *Ann. Rev. Neurosci.* 12:491–516.
Cepko et al. (1996) *PNAS USA*, 93:589–595.
Libby (1997) "Anatomical and Functional Characterization of Laminins in the Adult and Developing Vertabrate Retina" Dissertation.
Rousselle et al. (1991) *J. Cell Biol.*, 114:567–576.
Sugiyama et al. (1995) *Eur. J. Biochem.*, 228:120–128.
Balkema (1991) *J. Comp. Neurol.*, 312:573–583.
Balkema et al. (1996) *J. Neurocytol.*, 25:565–571.
Noakes et al. (1995) *Nature*, 374:258–262.
Miner et al. (1995) *J. Biol. Chem.*, 270:28523–28526.

* cited by examiner

*Primary Examiner*—Christina Chan
*Assistant Examiner*—F. Pierre VanderVegt
(74) *Attorney, Agent, or Firm*—Fish & Richardson

(57) ABSTRACT

The present invention features two members of laminin family, i.e., laminin 13 and laminin 14, the methods of making these molecules, and the methods of using these molecules in treating neural disorders, e.g., retinal disorders. The present invention also features using a preparation of laminin 5 to treat neural disorders, especially disorders associated with retina.

10 Claims, No Drawings

LAMININ 5, 13 AND 14 AND USES THEREOF

This application claims the benefit of previously filed Provisional Application No. 60/104,044 filed Oct. 13, 1998, and Provisional Application No. 60/104,430 filed Oct. 15, 1998 which are hereby incorporated by reference.

BACKGROUND OF THE INVENTION

The invention relates to two novel laminins, i.e., laminin 13 and 14, and methods of making and using these molecules. The invention also relates to the use of laminin 5 to treat neural disorders, e.g., to induce or promote retinal adhesion and the viability of retina photoreceptors.

The laminins are large heterotrimeric glycoproteins of the extracellular matrix. Each laminin heterotrimer is composed of an α, a β, and a γ chain, chosen from a number of possible homologues of each chain. Currently, eleven laminin chains have been identified: five α chains, three β chains, and three γ chains (reviewed in [1]).

SUMMARY OF THE INVENTION

The invention is based, in part, on the discovery of two novel members of the laminin family, laminin 13 and laminin 14. Accordingly, the invention features a purified or isolated preparation, a recombinant preparation, or a composition of laminin 13, which includes laminin chains α3, β2, and γ3. In a preferred embodiment, the laminin 13 is a trimer of an α3, β2, and γ3 chain.

In a preferred embodiment, the α3 chain has a molecular weight of about 300 kD, 200 kD, or 165 kD, the β2 chain has a molecular weight of about 190 kD or 170 kD, the γ3 chain has a molecular weight of about 200 kD or 170 kD.

In another preferred embodiment, the α3 chain is reactive or specifically binds to mouse monoclonal antibody BM-2 or any other antibody which can compete for the BM-2 epitope. In another preferred embodiment, the β2 chain is reactive or specifically binds to guinea pig polyclonal GP1 [47], mouse monoclonal C4 [46], R49, D5, D79, or any other antibody which can compete for the GP1 or C4 epitope.

In another aspect, the invention features, a purified or isolated preparation, a recombinant preparation, or a composition of laminin 14, which includes laminin chains α4, β2, and γ3. In a preferred embodiment, the laminin 13 is a trimer of an α4, β2, and γ3 chain.

In a preferred embodiment, the α4 chain has a molecular weight of about 185 kD, the β2 chain has a molecular weight of about 190 kD or 170 kD the γ3 chain has a molecular weight of about 200 kD or 170 kD.

In another preferred embodiment, the α4 chain is reactive or specifically binds to a α4 rabbit polyclonal antibody disclosed in J. Cell Biol 1997, 137:685–701 or any other antibody which can compete for the epitope of the α4 rabbit polyclonal antibody. In another preferred embodiment, the β2 chain is reactive or specifically binds to guinea pig polyclonal GP1 [47], mouse monoclonal C4 [46], R49, D5, D79, or any other antibody which can compete for the GP1 or C4 epitope.

The laminin chains of any laminin as disclosed herein can be the initial translation product or a degradation product, e.g., a naturally occurring degradation product of a laminin chain.

In another aspect, the invention features a composition which includes a purified isolated or recombinant laminin 13, 14, or both. The invention includes pharmaceutical preparations, e.g., a pharamaceutical preparation which include a pharmaceutically acceptable carrier.

In another aspect, the invention features an isolated nucleic acid, e.g., DNA, RNA, or cDNA encoding laminin 13. The isolated nucleic acid can be a combination of nucleic acids each encoding one or more laminin chains or a single nucleic acid. The isolated nucleic acid can be expressed in a vector, e.g., an expression vector or expressed directly in a cell. A vector containing a sequence corresponding to the sequence of the isolated nucleic acid can express the isolated nucleic acid in a suitable cell or a suitable in vitro environment.

The invention also features an isolated nucleic acid, e.g., DNA, RNA, or cDNA encoding laminin 14. The isolated nucleic acid can be a combination of nucleic acids each encoding one or more laminin chains or a single nucleic acid. The isolated nucleic acid can be expressed in a vector, e.g., an expression vector or expressed directly in a cell. A vector containing a sequence corresponding to the sequence of the isolated nucleic acid can express the isolated nucleic acid in a suitable cell or a suitable in vitro environment.

In another aspect, the invention features a recombinant laminin 13 or laminin 14 which can be produced, e.g., by expressing the laminin chains of laminin 13 or laminin 14 in a suitable cell host and under a condition suitable for the laminin chains to form laminin 13 or laminin 14.

In a preferred embodiment, the laminin 13 differs from a naturally occurring laminin 13 at at least 1, but less than 5, 10, or 15 amino acid residues. In another embodiment, one, two, or each laminin chain of a laminin, differs from its naturally occurring counterpart at at least 1, but less than 5, 10, or 15 amino acid residues.

In a preferred embodiment, the laminin 14 differs from a naturally occurring laminin 14 at at least 1, but less than 5, 10, or 15 amino acid residues. In another embodiment, one, two, or each laminin chain of laminin 14, differs from its naturally occurring counterpart at at least 1, but less than 5, 10, or 15 residues.

In another aspect, the invention features, a method of isolating a laminin 13 or 14. The method includes:

providing retinal tissue, e.g., a tissue selected from the group consisting of retina interphotoreceptor matrix, retina outer plexiform layer, neural retina, Müller cell, and a preparation of retinal neurons, and isolating the laminin 13, 14, or a preparation of both. The laminins can be isolated by the use of immuno affinity columns which use one or more mabs which are specific for the subunits of laminin 13 or 14.

In another aspect, the invention features, a method for producing laminin 13. The method includes:

providing recombinant nucleic acid which encodes a laminin α3 chain, a laminin β2 chain, and a laminin γ3 chain, and expressing the nucleic acid to provide recombinant laminin 13.

In a preferred embodiment a single cell includes nucleic acid which encodes the laminin α3 chain, a laminin chain β2, and a laminin γ3 chain.

In another aspect, the invention features, a method for producing laminin 14. The method includes:

providing recombinant nucleic acid which encodes a laminin α4 chain, a laminin β2 chain, and a laminin γ3 chain, and expressing the nucleic acid to provide recombinant laminin 13.

In a preferred embodiment a single cell includes nucleic acid which encodes the laminin α4 chain, laminin β2 chain, and laminin γ3 chain.

The invention still provides a method for treating a disorder associated with abnormal functions of synapses, e.g., insufficient stability, viability, formation, or defective organization of synapses. The method comprises administering to a subject an effective amount of laminin 13, laminin 14, laminin 5, separately or in combination with one another.

The invention provides a method for treating a disorder associated with inadequate neural cell growth, healing and regeneration,e.g., axon outgrowth, a disorder associated with abnormal subretinal space or interphotoreceptor matrix (IPM) such as inadequate stability of IPM, a disorder associated with retina contact, continuity, and/or adhesion, a disorder associated with abnormal or insufficient formation of synapses, and a disorder associated with viability of a neural cell, e.g., photoreceptor or an element thereof, e.g., outer segment, inner segment, cell body, and synapses. The method comprises administering to a subject an effective amount of laminin 13, laminin 14, laminin 5, separately or in combination with one another.

Still yet another feature of the present invention provides a method to treat a disorder associated with retinal abnormality, e.g., rod dystrophy, rod-cone dystrophy, macular degeneration, and retinal detachment. The method includes administering to a subject an effective amount of laminin 13, laminin 14, laminin 5, separately or in combination with one another.

Another feature of the present invention provides a method to induce neural cell growth or regeneration, e.g., axon outgrowth. The method includes administering to a subject an effective amount of laminin 13, laminin 14, laminin 5, alone or in combination with one another.

In a preferred embodiment, the method includes administering to a wound an effective amount of laminin 13, laminin 14, laminin 5, alone or in combination with one another.

Still another feature of the present invention provides a method to promote a condition, e.g., promote retina interphotoreceptor matrix stability, promote the stability of retina photoreceptor or an element thereof,e.g., outer segment, inner segment, cell body, and synapses, promote retina contact, continuity, and/or adhesion, promote the stability of synapses, and promote the formation of synapses. The method includes administering an effective amount of laminin 13, laminin 14, laminin 5, alone or in combination with one another.

Yet another feature of the present invention provides a method for preparing an implant, e.g., an implantable catheter, a retinal implant, a timed releasing device, a neural cell growth guide, an artificial tissue, an implant of the central nervous system, and an implant of the peripheral nervous system. The method includes contacting, e.g., coating or incubating the implant with laminin 5, 13, 14, alone or in combination with one another.

In a preferred embodiment, the implant is a subretinal implant, e.g., subretinal microphotodiodes, a visual prostheses, an implant for photoreceptor replacement, or a MPDA implant, e.g., as described in the abstract entitled "Can Subretinal Microphotodiodes Successfully Replace Degenerated Photoreceptors?" submitted by E. Zrenner et al at the Vision Research Conference held on May 9, 1998.

In another aspect, the invention features, a method of treating a disorder in a subject. The method includes: administering to the subject, an effective amount of laminin 13, laminin 14, or both.

In a preferred embodiment the disorder is: a disorder characterized by an insufficient level of a laminin, e.g., laminin 5, 13 or 14; a neural disorder; a disorder associated with neural tissue; disorder associated with abnormal functions of a synapse, e.g., insufficient stability, viability, formation, or the defective organization of a synapse; a disorder associated with inadequate neural cell growth, healing, or regeneration, e.g.,axon outgrowth; a disorder associated with abnormal subretinal space or interphotoreceptor matrix (IPM) such as inadequate stability of IPM; or a disorder associated with inadiquate viability of a neural cell, e.g., photoreceptor.

In a preferred embodiment the disorder is: a disorder associated with inadequate or insufficient contact, contunity, and/or adhesion between two structures, e.g., between a first and a second cell, e.g., a first and second neural cell, a first and second neural tissue, a first and second neural organ, e.g., brain and spinal cord, and a cell, e.g., a neural and a substrate, e.g., a membrane, and neural membranes or structures.

In a preferred embodiment the disorder is associated with a defect in retinal adhesion.

In a preferred embodiment the disorder is rod dystrophy, rod cone dystrophy, macular degeneration, or retinal detachment.

In preferred embodiments the laminin administered is laminin 13.

In preferred embodiments the laminin administered is laminin 14.

In another aspect, the invention features a method of treating a disorder in a subject. The method includes administering to said subject, an effective amount of laminin 5.

In a preferred embodiment the disorder is: a disorder characterized by an insufficient level of a laminin, e.g., laminin 5, 13, or 14; a neural disorder; a disorder associated with neural tissue; disorder associated with abnormal functions of a synapse, e.g., insufficient stability, viability, formation, or the defective organization of a synapse; a disorder associated with inadequate neural cell growth, healing, or regeneration, e.g., axon outgrowth; a disorder associated with abnormal subretinal space or interphotoreceptor matrix (IPM) such as inadequate stability of IPM; or a disorder associated with inadequate viability of a neural cell, e.g., photoreceptor.

In a preferred embodiment the disorder is: a disorder associated with inadequate or insufficient contact, contunity, and/or adhesion between two structures, e.g., between a first and a second cell, e.g., a first and second neural cell, a first and second neural tissue, a first and second neural organ, e.g., brain and spinal cord, and a cell, e.g., a neural and a substrate, e.g., a membrane, and neural membranes or.

In a preferred embodiment the disorder is associated with retina adhesion,

In a preferred embodiment the disorder is rod dystrophy, rod cone dystrophy, macular degeneration, or retinal detachment.

In another aspect, the invention features a method of increasing the stability of a biological structure. The method includes contacting the structure with an effective amount of laminin 13 or 14.

In preferred embodiments the method is performed: in vivo, e.g., on a human or animal subject; in vitro, e.g., on a cultured tissue or cell; ex vivo, e.g., on an tissue which will be implanted in a subject.

In preferred embodiments the structure comprises: the retina, or a component thereof, e.g., the retina interphotoreceptor matrix, a photoreceptor or an element thereof, e.g., outer segment, inner segment, cell body, and synapses; a neuron or synapse, or a tissue which includes a neuron or a synapse; a nerve fiber; and the spinal cord.

In another aspect, the invention features a method of increasing the stability of a synapse. The method includes contacting the synapse or a cell which forms the synapse with an effective amount of laminin 13, 14, or a combination thereof.

In a preferred embodiment, the synapse is a synapse of the central nervous system, or a synapse of the peripheral nervous system.

In preferred embodiments the laminin administered is laminin 13.

In preferred embodiments the laminin administered is laminin 14.

In another aspect, the invention features a method of increasing the stability of a biological structure. The method includes contacting the structure with an effective amount of laminin 5.

In preferred embodiments the method is performed: in vivo, e.g., on a human or animal subject; in vitro, e.g., on a cultured tissue or cell; ex vivo, e.g., on an tissue which will be implanted in a subject.

In preferred embodiments the structure comprises: the retina, or a component thereof, e.g., the retina interphotoreceptor matrix, a photoreceptor or an element thereof, e.g., outer segment, inner segment, cell body, and synapses; a neuron or synapse, or a tissue which includes a neuron or a synapse; a nerve fiber; the spinal cord.

In another aspect, the invention features a method of increasing the stability of a synapse. The method includes contacting the synapse or a cell which forms the synapse with an effective amount of laminin 5.

In a preferred embodiment, the synapse is a synapse of the central nervous system, or a synapse of the peripheral nervous system.

In another aspect, the invention features a method of promoting the contact, continuity, or adhesion of a first structure and a second structure. The method includes contacting at least one of the structures with an effective amount of laminin 13, 14, or both.

In a preferred embodiment: the first structure can be any of a cell, a membrane, a tissue, an organ, or a nerve fiber, and the second structure can be any of a cell, a membrane, a tissue, an organ, or a nerve fiber.

In a preferred embodiment, the first structure is a retinal cell and the second structure is a retinal cell.

In a preferred embodiment the first structure is a cell, e.g., a neural cell and the second structure is a substrate, e.g., a membrane.

In a preferred embodiment the first structure is a cell, tissue, or an organ, e.g., a neural cell, a nerve, brain, spinal cord, or a membrane and the second structure is a substrate, e.g., a surface of an implant, e.g., a prosethetic device, or an in vivo or ex vivo substrate, e.g., a substrate on which a cell or tissue is cultured.

In preferred embodiments the method is performed: in vivo, e.g., on a human or animal subject; in vitro, e.g., on a cultured tissue or cell; ex vivo, e.g., on an tissue which is implanted in a subject.

In preferred embodiments the structure comprises: the retina, or a component thereof, e.g., the retina interphotoreceptor matrix, a photoreceptor or an element thereof; a neuron or synapse, or a tissue which includes a neuron or a synapse; a nerve fiber; and the spinal cord.

In another aspect, the invention features a method of promoting retinal contact, continuity, or adhesion in a subject. The method includes administering an effective amount of laminin 13, 14, or both.

In a preferred embodiment the laminin is provided with a pharmaceutically acceptable carrier.

In a preferred embodiment an integrin is also administered.

In another aspect, the invention features a method for treating a subject having a retinal disorder, e.g., a disorder associated with insufficient retinal contact, continuity, and/or adhesion or retinal degeneration. The method includes administering to a subject an effective amount of laminin 13, 14 or both.

In a preferred embodiment, the disorder is: rod dystrophy, rod-cone dystrophy, macular degeneration, retinal detachment, or retinitis pigmentosa.

In preferred embodiments the laminin administered is: laminin 13.

In preferred embodiments the laminin administered is: laminin 14.

In another aspect, the invention features a method of stimulating the formation of a synapse. The method includes contacting the synapse, or a cell which forms the synapse with an effective amount of laminin 13, 14 or both.

In a preferred embodiment, the synapse is a synapse of the central nervous system, or a synapse of the peripheral nervous system.

In another aspect, the invention features a method of promoting the contact, continuity, or adhesion of a first structure and a second structure. The method includes contacting at least one of the structures with an effective amount of laminin 5.

In a preferred embodiment: the first structure can be any of a cell, a membrane, a tissue, an organ, or a nerve fiber, and the second structrue structure can be any of a cell, a membrane, a tissue, an organ, or a nerve fiber.

In a preferred embodiment, the first structure is a retinal cell and the second structure is a retinal cell.

In a preferred embodiment the first structure is a cell, e.g., a neural cell and the second structure is a substrate, e.g., a membrane.

In a preferred embodiment the first structure is a cell a tissue, or an organ, e.g., a neural cell, a neural tissue, brain, spinal cord, a nerve, or a membrane and the second structure is a substrate, e.g., a surface of an implant, e.g., a prosethetic device, or an in vivo or ex vivo substrate, e.g., a substrate on which a cell or tissue is cultured.

In preferred embodiments the method is performed: in vivo, e.g., on a human or animal subject; in vitro, e.g., on a cultured tissue or cell; ex vivo, e.g., on an tissue which is implanted in a subject.

In preferred embodiments the structure comprises: the retina, or a component thereof, e.g., the retina interphotoreceptor matrix, a photoreceptor; a neuron or synapse, or a tissue which includes a neuron or a synapse; a nerve fiber; and the spinal cord.

In another aspect, the invention features a method of promoting retinal contact, continuity, or adhesion in a subject. The method includes administering an effective amount of laminin 5.

In a preferred embodiment the laminin is provided with a pharmaceutically acceptable carrier.

In a preferred embodiment an integrin is also administered.

In another aspect, the invention features a method for treating a subject having a retinal disorder, e.g., a disorder associated with insufficient retinal contact, continuity, and/or adhesion or retinal degeneration. The method includes administering to a subject an effective amount of laminin 5.

In a preferred embodiment, the disorder is: rod dystrophy, rod-cone dystrophy, macular degeneration, retinal detachment, or retinitis pigmentosa.

In another aspect, the invention features a method of stimulating the formation of a synapse. The method includes contacting the synapse, or a cell which forms the synapse with an effective amount of laminin 5.

In a preferred embodiment, the synapse is a synapse of the central nervous system, or a synapse of the peripheral nervous system.

In another aspect, the invention features a method of increasing the viability of retina photoreceptors or a component thereof, e.g., outer segment, inner segment, cell body, and synapses. The method includes contacting the retina photoreceptors with an effective amount of one or more of laminin 5, 13, or 14.

In a preferred embodiment an integrin is also administered.

In another aspect, the invention features a method for promoting neural cell growth, healing, or regeneration, e.g., axon outgrowth. The method includes contacting the neural cell with an effective amount of one or more of laminin 13, 14, or 5.

In preferred embodiments the method is performed: in vivo, e.g., on a human or animal subject; in vitro, e.g., on a cultured tissue or cell; ex vivo, e.g., on an tissue which will be implanted in a subject.

Other features and advantages of the invention will be apparent from the following detailed description, and from the claims.

DETAILED DESCRIPTION

The invention features two novel members of laminin family, i.e., laminin 13 and laminin 14, and the methods of making and using these novel laminins. The invention provides method of using laminin 5, e.g., in neural associated disorders.

As used herein the term "administering" refers to delivery of a preparation, composition, an active portion, or an active fragment of laminin 13, 14, 5, alone, in combination with each other and/or with one or more other compounds or preparation.

Administration of laminins 13, 14, 5, alone or in combination with one another can include local or systemic administration, including injection, oral administration, particle gun, or catheterized administration, and topical administration. Various methods can be used to administer the therapeutic composition of laminins 13, 14, 5, alone or in combination with one another directly to a specific site in the body. For example, a small neural wound can be located and the therapeutic composition can be applied, e.g., several times in several different locations, within the wound. The therapeutic laminin compositions can be directly administered to the surface of a neural wound, for example, by topical application of the composition. X-ray imaging can be used to assist in certain of the above delivery methods. Combination therapeutic agents, including a laminin 13, 14, or 5 protein or polypeptide or a subgenomic laminin polynucleotide and other therapeutic agents, can be administered simultaneously or sequentially.

Receptor-mediated targeted delivery of therapeutic compositions containing laminin 13, 14, and/or 5 subgenomic polynucleotides to specific tissues can also be used. Receptor-mediated DNA delivery techniques are described in, for example, Findeis et al. (1993), *Trends in Biotechnol.* 11, 202–05; Chiou et al. (1994), *Gene Therapeutics: Methods and Applications of Direct Gene Transfer* (J. A. Wolff, ed.); Wu & Wu (1988), *J. Biol. Chem.* 263, 621–24; Wu et al. (1994), *J. Biol. Chem.* 269, 542–46; Zenke et al. (1990), *Proc. Natl. Acad. Sci. U.S.A.* 87, 3655–59; Wu et al. (1991), *J. Biol. Chem.* 266, 338–42.

Alternatively, a laminin therapeutic composition can be introduced into human cells ex vivo, and the cells then replaced into the human. Cells can be removed from a variety of locations including, for example, from a selected neural tissue or from an affected organ.

Both the dose of the laminin composition and the means of administration can be determined based on the specific qualities of the therapeutic composition, the condition, age, and weight of the patient, the progression of the disease, and other relevant factors. If the composition contains laminin 13, 14, and/or laminin 5 protein or polypeptide, effective dosages of the composition are in the range of about 5 $\mu$g to about 50 $\mu$g/kg of patient body weight, about 50 $\mu$g to about 5 mg/kg, about 100 $\mu$g to about 500 $\mu$g/kg of patient body weight, and about 200 to about 250 $\mu$g/kg.

Therapeutic compositions containing laminin 13, 14, and/or 5 subgenomic polynucleotides can be administered in a range of about 100 ng to about 200 mg of DNA for local administration in a gene therapy protocol. Concentration ranges of about 500 ng to about 50 mg, about 1 $\mu$g to about 2 mg, about 5 $\mu$g to about 500 $\mu$g, and about 20 $\mu$g to about 100 $\mu$g of DNA can also be used during a gene therapy protocol. Factors such as method of action and efficacy of transformation and expression are considerations that will effect the dosage required for ultimate efficacy of the laminin 13, 14, and/or 5 subgenomic polynucleotides. Where greater expression is desired over a larger area of tissue, larger amounts of laminin 13, 14, and/or 5 subgenomic polynucleotides or the same amounts readministered in a successive protocol of administrations, or several administrations to different adjacent or close tissue portions of for example, a tumor site, may be required to effect a positive therapeutic outcome. In all cases, routine experimentation in clinical trials will determine specific ranges for optimal therapeutic effect.

The term "effective amount" means the amount that is sufficient to reduce or alleviate at least one adverse effect or symptom of a disorder. Such amount is determinable by one skilled in the art, e.g., based on the disease stage, age, sex, and weight of the to be treated subject and the condition of the treatment. As a reference, the amount administered can be at a concentration of at least from about 0.1 to 500 $\mu$g/ml, from about 1 to 200 $\mu$g/ml, from about 10 to 150 $\mu$g/ml, or from about 10 to 100 $\mu$g/ml.

The term "purified" or "substantially pure" or isolated "preparation" means a polypeptide or protein that has been separated from other proteins, lipids, and nucleic acids with which it naturally occurs. Preferably, the polypeptide or protein is also separated from substances, e.g., antibodies or gel matrix, e.g., polyacrylamide. Preferably, the polypeptide constitutes at least 10, 20, 50, 70, 80 or 95% dry weight of the purified preparation.

The term "subject" as used herein refers to a mammal. Examples of mammals include human and nonhuman primates, e.g., a monkey, a goat, or a rodent, e.g., a rat or a mouse, having a disorder associated with insufficient laminin, e.g., laminin 5, 13, and/or 14-activity. The mammal is preferably a primate, e.g., a human.

The term "stability" means structural, anatomic molecular, and/or functional integrity, intactness, or completeness which is testable or observable by any suitable means. For example, the stability of retina photoreceptor can be tested by ERG, e.g., indicated by a wave and b wave.

The term "pharmaceutically acceptable carrier" is intended to include a solvent, dispersion media, coatings, antibacterial and antifungal agents, isotonic and absorption delaying agents, and the like, compatible with pharmaceutical administration. The use of such media and agents for pharmaceutically active substances is well known in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier.

Typically, the therapeutic laminin composition is prepared as an injectable, either as a liquid solution or suspension; however, solid forms suitable for solution in, or suspension in, liquid vehicles prior to injection can also be prepared. The composition can also be formulated into an enteric coated tablet or gel capsule according to known methods in the art, such as those described in U.S. Pat. No. 4,853,230, EP 225,189, AU 9,224,296, and AU 9,230,801.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Laminins 13 and 14

Components of the extracellular matrix exert myriad effects on tissues throughout the body. In particular, the laminins, a family of heterotrimeric extracellular glycoproteins affect tissue development and integrity in such diverse organs as the kidney, lung, skin, and nervous system. Of these, we have focused on the roles that laminins play in the differentiation and maintenance of the nervous system. Below, we demonstrate the presence of laminins within a component of the central nervous system, the retina. Within the retina, we have found four laminin. chains: α3, α4, β2, and γ3. All four chains are co-expressed in two locations: the matrix surrounding photoreceptors and the layer in which photoreceptors make synaptic contacts with retinal interneurons. Thus, we have identified two novel laminin heterotrimers in the central nervous system, which we here term laminin-13 (α3β2γ3) and laminin-14 (α4β2γ3). These laminins play a role in photoreceptor stability and synaptic organization.

One of the most widely studied components of the central nervous system is the retina, frequently cited as an ideal model system for extrapolation to the rest of the central nervous system. Here, we have assembled reagents to the eleven known laminin chains to identify which chains are present in the neural retina, in order to identify which laminin trimers are present. Our identification of several laminin chains in the IPM and plexiform layers allows us to determine the existence of at least 2 additional laminins: laminin-13 and laminin-14, that are important in maturation and stability in the central nervous system.

Experimental Materials and Procedures
a. Immunohistochemistry

Immunohistochemistry was performed as previously described [33,45]. Adult rat eyecups were embedded in O.C.T. compound (Miles, Elkhart, IN) and frozen by immersion in liquid nitrogen-cooled isopentane. Transverse, 10 μm-thick sections were cut with a Leica cryostat and placed onto Superfrost Plus slides (Fisher, Pittsburgh, Pa.). Unfixed transverse sections of human retina were supplied by A. Milam (University of Washington, Seattle, Wash.). Slides were stored at −20° C. until use. For use, slides were returned to room temperature, were washed in phosphate-buffered saline (PBS; 137 mM NaCl, 2.68 mM KCl, 10 mM $Na_2HPO_4$, 1.76 mM $KH_2PO_4$, pH 7.4), and then incubated in primary antibodies for two hours at room temperature or overnight at 40° C. Primary antibodies (see below) were diluted in PBS containing 2% goat serum, 2% bovine serum albumin, or both. Sections were washed in PBS and incubated in species-appropriate, affinity-purified, fluorescently-labelled secondary antibodies diluted in 2% goat serum in PBS for 1 hour at room temperature. Following washes in PBS, slides were mounted in 90% glycerol and 10% water, containing paraphenylenediamine (1 mg/ml; Sigma, St. Louis, Mo.) to reduce photobleaching.

The antibodies used were: laminin-1 (Life Technologies; rabbit polyclonal); laminin α2 (Life Technologies; mouse monoclonal); laminin α3 (BM-2, mouse monoclonal); laminin α4 ([2]; rabbit polyclonal), laminin α5 ([2]; rabbit polyclonal); laminin β1 (C21, [46]; mouse monoclonal); laminin β2 (GP1, [47]; guinea pig polyclonal and C4, [46]; mouse monoclonal); laminin β3 (6F12, [48]; mouse monoclonal); laminin γ7 (D18, [47]; mouse monoclonal); laminin γ2 ([49]; rabbit polyclonal); laminin γ3 (rabbit polyclonal).

b. In situ Hybridizations

Adult rat eye cups were dissected and fixed overnight at 4° C. in 4% paraformaldehyde in PBS (pH 7.4), dehydrated, and embedded in paraffin. Fifteen micron-thick sections were cut and placed onto Probe-on Plus slides (Fisher). Fixed, adult, human retinae were obtained as frozen sections from A. Milam (University of Washington). Rehydrated rat sections or frozen human sections were then processed for in situ hybridizations as previously described [45].

cRNA probes for the laminin chains were generated as previously described [45]. Probes for laminin β1 and β2 and for cellular retinaldehyde binding protein were those used previously [45]. A CRNA probe for laminin α5 [50] was generated from a plasmid obtained from J. Sanes (Washington University, Saint Louis, Mo.). All other laminin probes were generated from plasmids (containing fragments of human laminin cDNAs) obtained from R. Burgeson (Harvard Medical School, Charlestown, Mass.). cRNAs were labeled during transcription by the incorporation of digoxigenin-UTP (Boehringer Mannheim, Indianapolis, Ind.); ca. 1 μg/ml of cRNA was used for hybridization.

Laminin Protein Expression

Antibodies which recognize the eleven known laminin chains were used to catalog the laminin chains in adult rat and human retinae. We describe here the reactivity for antibodies directed against each of these chains.
a. Laminin Alpha Chains A polyclonal antiserum which recognizes the three chains of laminin-1 (α1, β1, and γ1) reacts only with the vasculature in the rat and human, and not with components of the neural retina. This observation suggests that the laminin α1 chain, a component of laminin-1, is not associated with the matrix of either the neural retina or the IPM. Laminin-1 is a well-characterized component of both true basement membranes of the retina, i.e., the inner limiting membrane and Bruch's membrane (see [33] for example).

Laminin α2, is also present in the retinal vasculature. We did not detect laminin α2 associated with ganglion cell bodies or in the inner limiting membrane, when this structure was intact.

Laminin α3 is present in the interphotoreceptor matrix: laminin α3 is prominent at the external limiting membrane and at the tips of the photoreceptor inner segments. Laminin α3 immunoreactivity is also present in the outer plexiform layer. It is clear that laminin α3 is associated with the neural retina and is, thereby, a partner for laminin β2. In the human, weak immunoreactivity for laminin α3 is also present surrounding cell bodies of the outer and inner nuclear layers. Finally, in human, laminin α3 is diffusely associated with the inner plexiform layer.

In contrast to laminins α1–3, laminin α4 appears to have a broad distribution in rat and human retinae. Immunoreactivity for laminin α4 is present in the IPM, as well as diffusely in both the inner and outer plexiform layers. This extensive immunoreactivity in both plexiform layers, and the lack of any association with the retinal vasculature, suggests that laminin α4 is contained within the extracellular matrix of the plexiform layers. However, the most prominent reactivity for laminin α4 is in what appear to be Müller cell fibers coursing through the retina. These fibers have been confirmed as Müller cell processes, based on co-localization of laminin α4 with a Müller cell marker (vimentin). Reactivity for laminin α4 is also present in the ganglion cell layer; this may reflect laminin α4 associated with the endfeet of Müller cells. The presence of laminin α4 within the Müller cell suggests that the Müller cell is a source of laminin α4 in the neural retina, consistent with the data that confirmed the Müller cell as a source of another laminin chain, β2 [45].

The only antiserum available against laminin α5 [2] does not cross-react with human laminin α5. However, in the rat, laminin α5, like laminins α1 and 2, does not appear to be associated with the neural retina per se, but rather associated with retinal vasculature. Laminin α5 immunoreactivity is present in the choroid, the hyaloid vessels, the outer plexiform layer vessels and the vasculature which extends through the retina from the hyaloid vessels to the outer plexiform layer.

Together, these data show that all five laminin a chains are expressed in the retina, but three-laminins α1, 2, and 5—may be associated exclusively with the retinal vasculature of these, laminin α1 has not been directly associated with the basement membrane of vessels; indeed, protein transfer blots of retinal extracts fail to detect the α1 chain [18]. In the case of laminin α2, these data conflict somewhat with previous reports of expression in some vertebrates [32], although they are consistent with others [51] that show that laminin α2 is restricted to the vasculature in the human retina. In contrast to these three laminin α chains, two-laminins α3 and 4—are associated with the IPM and, potentially, both are associated with the neural retina at synapses in the plexiform layers. Laminins at each of these locations could be provided from the cell that spans the entire thickness of the retina, the Müller cell; the Müller cell is the likely source for at least one other laminin chain, β2 [45].

b. Laminin Beta Chains

As noted above, a polyclonal serum that recognizes all three chains of laminin-1, including laminin β1, reacts only with the vasculature in rat and human retinae. Thus, laminin β1 can not be an element of the matrix of either the IPM or the neural retina. A rat-reactive antibody against the ⊕1 chain confirms this observation. However, as there is little authentic laminin α1 in the retina, and little authentic laminin β1 in the retinal vasculature of the rat, it is likely that the polyclonal serum against laminin-1 is detecting laminin γ1 in the vasculature of both rat and human.

Laminin β2 is present in the interphotoreceptor matrix, and appears to be associated with the external limiting membrane. Here, we also demonstrate a similar distribution in the human retina. Laminin β2, a known component of brain vasculature [24], was also associated with the vessels of the retina. In the human, immunoreactivity is also present surrounding cell bodies in the inner nuclear layer, as well as in the inner limiting membrane. In both species, laminin β2 is also diffusely associated with the outer plexiform layer. A comparison of this diffuse immunoreactivity to that for laminin-1 or laminin α2 suggests that laminin β2 is not only associated with the vasculature within the outer plexiform layer. Laminin β2 is localized to synapses in the central nervous system, as it is in the peripheral nervous system [43].

Laminin β3 immunoreactivity was not present in the rat retina, and is only present in the vasculature of the human retina. As laminin β3 has a "tightly restricted tissue distribution" in rodent [52], the relative paucity of laminin β3 in the retina is not surprising.

Together, these data show that, although laminins β1 and 3 are associated with the basement membrane of the retinal vasculature, only one β chain—laminin β2—is expressed in the matrix of the IPM. Moreover, laminin β2 is also expressed in the matrix of the outer plexiform layer.

c. Laminin Gamma Chains

As noted above, a polyclonal serum that recognizes all three chains of laminin-1, including laminin γ1, reacts largely with the vasculature. Consistent with this observation, an antibody directed against laminin γ1 reacts only with the vasculature in both rat and human, suggesting that the anti-laminin-1 serum is reacting with at least the γ1 chain. In addition, in the human, laminin γ1 is present at the internal limiting membrane; this may reflect production by astrocytes, the hyaloid blood vessels, and retinal ganglion cells ([30]; compare [53]). There is also some punctate immunoreactivity for laminin γ1 within the ganglion cell layer. Importantly, there is no laminin γ1 reactivity in the IPM or plexiform layers; thus, laminin γ1 is confined to the vitread side of the retina.

The laminin γ2 chain is not within the IPM, neural retina, or the vasculature. This lack of expression is consistent with previous reports that have suggested a restricted distribution of laminin γ2 [54].

Laminin γ3 is the most recently isolated of the growing family of laminins. RNA hybridization analysis (Northern blots) suggests that laminin γ3 is expressed in several tissues including brain, testis, ovary, and lung. Here, we report the presence of laminin γ3 in a portion of the central nervous system. Prominent laminin γ3 immunoreactivity is seen in the IPM; notably, throughout the region of photoreceptor inner segments. In addition, there is marked laminin γ3 immunoreactivity associated with the external limiting membrane in the rat and surrounding cell bodies within the outer and inner nuclear layers in the human. Finally, diffuse laminin γ3 is also present in the outer plexiform layer, at least in the rat. As with laminin α3, α4, and β2, we cannot say conclusively that the laminin γ3 immunoreactivity in the outer plexiform layer is associated with the synaptic components of the outer plexiform layer. However, laminin γ3 is not associated with the vasculature present at the vitread side of the retina, and its pattern of expression is distinct from that for laminin chains in the vasculature, such as γ1. Therefore, it is probable that the laminin γ3 in the outer plexiform layer is contained within the matrix of the plexiform layer.

Together, these data show that laminin γ3 is the only known laminin γ chain in the IPM. Furthermore, laminin γ3 appears to be the only laminin γ chain found associated with the synaptic regions of the outer plexiform layer.

In summary, we have shown the presence of four laminin chains: α4, α3, β2, and γ3 in the IPM. The lack of other β or γ chains in the IPM demonstrates that, in the IPM, there are two novel laminin trimers: α3β2γ3 and α4β2γ3. In the matrix of the outer plexiform layer, these same trimers appear to be present. In contrast, only one laminin chain, α4, is prominent in the matrix of the inner plexiform layer, suggesting that other, uncharacterized, β and γ chains may be expressed in the retina. Recently, preliminary reports have been made about both laminins β4 and γ4; thus, these molecules are likely candidates for the as yet identified IPL laminins.

Laminin RNA Expression cRNA probes which recognize the RNAs encoding the eleven known laminin chains were used to catalog these RNAs in the retina and to localize them to particular cell types. As laminin trimers are assembled prior to secretion (e.g., [15,55]), the RNAs encoding all three chains of any given trimer should be present in the same cell.

a. Laminin Alpha Chains

RNAs encoding the laminin α1 and α2 chains were not detected in the rat or human retina, suggesting that both of these RNAs are not abundant in the retina.

In contrast, the RNA encoding laminin α3 is detectable in the rat and human retina. Interestingly, laminin β3 RNA is not localized to perinuclear sites; rather, the RNA is in fibers coursing through the inner and outer nuclear layers and the outer plexiform layer. This location is consistent with production of laminin α3 RNA by Müller cells.

The RNA encoding laminin α4 is present in a pattern similar to that encoding laminin α3: there are no obvious perinuclear sites, but rather the RNA appears to be located in fibers coursing through the inner and outer nuclear layers. Unlike laminin α3, there does seem to be perinuclear staining around some cell bodies in the inner nuclear layer of the human retina, suggesting that the source of the RNA encoding laminin α4 is a cell in the inner nuclear layer. Again, this pattern is consistent with production of laminin α4 RNA by Müller cells. Finally, in human, laminin α4 RNA transcripts are present in the ganglion cell layer, in what we presume to be Müller cell endfeet.

Similar to laminins α1 and 2, RNA encoding laminin α5 is not detectable within the rat retina; this suggests that the RNA encoding laminin α5 is not abundant in the rat retina. In an example of species variation, we detected RNA encoding laminin α5 within the neural retina of the human. The pattern of expression for RNA encoding laminin α5 in the human retina is similar to, albeit considerably less intense than, that detected with a probe for laminin α4.

Together, the patterns of expression for the RNAs encoding the laminin a chains demonstrate that laminins α3 and 4 are expressed in the neural retina, consistent with the presence of laminins α3 and 4 protein noted above. Specifically, they suggest that laminins α3 and 4 are produced in the neural retina and deposited in the matrices of the IPM and outer plexiform layer, and, in the case of laminin α4, the inner plexiform layer. The presence of modest amounts of RNA encoding laminin α5 could not be correlated with the presence of laminin α5 protein in human retina, as, at the time of these experiments, no human-reactive laminin α5 antibodies were available. However, the lack of expression of laminin α5 in the rat suggests that there is no laminin α5 protein associated with the neural retina.

b. Laminin Beta Chains

RNA encoding laminin β1 is not expressed at levels detectable by our methods in the neural retina, as previously reported [45]. These data are consistent with the lack of laminin β1 protein in neural structures within the retina.

We have previously shown that laminin β2 is expressed in the adult rat retina [45]. Here we demonstrate that RNA encoding laminin β2 is present in fibers in the nuclear layer, possibly the Müller cell, is a source of laminin β2 in the neural retina. Finally, as shown here and previously [45] for the rat, and here for the human, this pattern of RNA expression is similar to that for cellular retinaldehyde binding protein, an authentic marker of the Müller cell [56]. Recently, we have obtained an immortalized rat muller cell line and we have shown that these cells make laminin β2 as well.

Laminin β3 RNA appears to be expressed in the adult rat retina: RNA encoding laminin β3 is located in fibers coursing through the inner and outer nuclear layers, in the outer plexiform layer, and at the outer limiting membrane. In another example of species variation, RNA encoding could not be detected within the human neural retina. Although RNA encoding laminin β3 seems to be present in the rat retina, its absence in the human retina, combined with the lack of laminin β3 protein in both species (see above), suggests that laminin β3 is not a prominent component of neural retinae.

Together, these data suggest that, in both rat and human, laminin β2 is the prominent β chain expressed in the neural retina. In addition, neither laminin β1 nor laminin β3 are likely to be expressed in the retina outside of the vasculature.

c. Laminin Gamma Chains

Neither laminin γ1 nor γ2 RNAs were detected in the neural retina. This suggests that the laminin γ1 protein in the internal limiting membrane is not derived from the neural retina. Laminin γ1 in the internal limiting membrane must, therefore, be derived from one of the non-neural retinal cells that contact it. Both astrocytes and the hyaloid vessel contact the internal limiting membrane and have been suggested as sources for protein components of the internal limiting membrane [30,53].

In contrast, RNA encoding laminin γ3 is present in both the rat and human retina. Laminin γ3 RNA is expressed in a pattern that is similar to that for laminins α3, α4, and β2: in fibers coursing through the outer nuclear layer, at the external limiting membrane, and in presumed Müller cell endfeet in the ganglion cell layer. The γ3 chain is, therefore, the likely γ component of laminins in both the IPM and the OPL. However, it is possible that in human retina, laminin γ3 is expressed by ganglion cells; in other parts of the central nervous system, laminin γ3 is expressed by projection neurons like ganglion cells (Brunken, unpublished observations).

In summary, the expression patterns for the laminin RNAs detected in the neural retina demonstrate that RNAs encoding the laminin α3, α4, β2, and γ3 chains are expressed in the rat and human retina. Although slightly different, the basic distribution of all of these RNAs was the same: largely within fibers coursing through the inner and outer nuclear layers. RNAs for laminin α4 and β2 also appear to be present at perinuclear sites in the inner nuclear layer as well as within the ganglion cell layer. Together, these data demonstrate that the Müller cell is the source of these laminin-encoding RNAs; in addition, they demonstrate that the retina produces two novel laminin trimers: laminin-13 (α3β2γ3) and laminin-14 (α4β2γ3).

SUMMARY

We have previously shown that a member of the laminin family, laminin β2, is present in the adult vertebrate retina [18,33,45]; in particular, we have shown that laminin β2 is a component of the IPM [18]. Here, we have assembled reagents to the known laminin chains in order to identify these potential partners for laminin β2 in the neural retina. In order to generalize our findings across species, we have performed our localizations in two mammalian species: rat and human. By comparing across the two, both for expression of protein and RNA, we have determined the complement of retinal laminins.

Together, our data demonstrate that at least four laminin chains are present in adult mammalian retina: α3, α4, β2, and γ3. This complement of individual laminin chains, and their co-localization, in the neural retina demonstrates the presence of at least two novel laminin trimers in the neural retina, which we here term laminin-13, composed of α3, β2, and γ3 chains, and laminin-14, composed of α4, β2, and γ3 chains. These new laminins appear to be expressed in at least two locations: the interphotoreceptor matrix and the outer plexiform layer. Laminins present therein are likely to serve unique functions, including the control of differentiation (in the interphotoreceptor matrix [18,19]) and, potentially, stabilization of synapses (in the outer plexiform layer; [57] manuscript in preparation; compare [44]).

a. Laminins in the IPM

Whereas heterotrimeric laminins have not, as yet, been biochemically isolated specifically from the IPM, we have previously provided evidence that laminin β2 is a component of the IPM of vertebrates [18]. Histologically, laminin β2 fills the space between the photoreceptors—the IPM—in en face sections of adult retina. Biochemically, laminin β2 is tightly associated with a matrix fraction of the adult retina, suggesting that it is a component of the IPM. Our immunohistochemical studies reported here, on rat and human retina, show three other laminin chains—laminins α3, α4, and γ3—surrounding inner segments, which is believed to reflect a location in the IPM. Changes in the complement of IPM laminins may be of relevance in several retina degenerations diseases. We believe that IPM laminins are important for mechanical stability and binding other insoluble elements of matrix (e.g., heparin sulfate proteoglycans like agrin) which in turn would bind and concentrate soluble growth factors (e.g, bFGF) in the proximal IPM. Thus, we believe that during the advanced stages of rod dystrophy there is an disruption in the expression of IPM which in turn produces a further corruption of the environment with negative consequences for the remaining photoreceptors. At the very least, a disruption of IPM laminins is believed to reduce retinal adhesion which will also negatively affect photoreceptor survival. Thus, alterations in laminin expression in various rod dystrophies, rod-cone dystrophies, and in macular degeneration should be undertaken.

b. Laminins in Retinal Synaptic Layers

Several laminin chains are present in the plexiform layers; in particular, laminins α3, α4, β2, and γ3 are expressed in the outer plexiform layer outside of the basment membranes of the retinal vasculature. Unfortunately, with light microscopy it is impossible to determine conclusively with which structures these chains are associated within the outer plexiform layer. For example, in addition to the synapses and vasculature in the outer plexiform layer, there are fibers of Müller cells [58] which could contain the proteins. However, with the exception of laminin α4 (see Results), none of the laminin chains is obviously within Müller cells in rat or human, suggesting that they are, in fact, associated with synapses. Moreover, co-localization of some laminins with a marker of the synapse has been achieved but the exact location of the laminin chains in the retinal synaptic layers awaits immunohistochemistry done at the electron microscopic level.

However, these data allow us to believe that laminins are present at the synapses between neurons in the central nervous system in a location analogous to that at the neuromuscular junction [43]. We believe that laminins are involved in the stabilization of synapses in the central nervous system.

c. Müller Cells Produce Retinal Laminins

The RNA encoding the laminin chains that are expressed in the neural retina are located in cells that span the retina. This location is consistent with the production of laminins by Müller cells [45]. Müller cell cytoplasm is spread across the retina [59] and RNA is distributed throughout these processes [60,61]. In addition, we have shown that the distribution of RNA encoding CRALBP, in both rat and human retina, is similar to that of the laminins: throughout the retina, in fibers coursing through the retinal cell layers. Together with the immunohistochemical data noted above, these data demonstrate a Müller cell source for laminins in the IPM. Moreover, our preliminary studies demonstrate that immortalized rat Müller cells produce at least laminins α3, α4, β2, and γ3 in culture.

d. Laminins in the Nervous System

In the peripheral nervous system, several cell types produce a variety of laminins. For example, the glial elements that wrap peripheral nerves, Schwann cells, have long been known to produce laminins [62,63], including at least one that contains the β2 chain [64]. Also in the periphery, muscle cells appear to express several different laminin trimers on their surface [43,47,68,2,69]. One laminin chain, α2, has been shown to be involved in murine and human muscular dystrophies: mutations in α2 have been found in murine muscular dystrophies [70,71] and in some cases of a human congenital muscular dystrophy [72].

Similarly, in the central nervous system, several laminin chains have been found in a variety of areas, particularly during development. The cellular sources of these laminin chains include all three major cell classes of the central nervous system: glia, neurons, and neuroglial progenitors. Glial cells, including astrocytes, Bergmann glia, and Müller cells, are thought to be a major source of laminins in the adult and developing CNS (see, for example, [73,17,74,64, 75,24,76,45].

In a particular portion of the CNS, the retina, we believe that laminins may be important in maintaining the proper environment for a particular class of cell, photoreceptors. We believe that laminins are involved in retinal adhesion.

Here, for the first time, a component of the central nervous system has been examined for the presence of all the known laminin chains. The use of two different species, and examination of both protein and RNA expression, allowed us to use reagents which, together, react with all the currently known laminin chains. Our data show that a component of the central nervous system, the retina, contains at least four laminin chains: α3, α4, β2, and γ3. The paucity of laminin γ1 and γ2, and the presence of two laminin a chains demonstrate that there are at least two novel laminin trimers in the CNS. We now refer to these potential new trimers as laminin-13 (α3β2γ3) and laminin-14 (α4β2γ3). Our immunoprecipitation studies using chain-specific antibodies demonstrate that laminin-14 exists as a heterotrimer in the retina.

Intriguingly, laminins-13 and -14 appear to be expressed in two locations: (1) within the interphotoreceptor matrix, and (2) in the outer plexiform layer. The location of these laminins in the outer plexiform layer demonstrates that they may serve to stabilize retinal synapses, in a manner analogous to that suggested for β2-containing laminins, perhaps including laminin-11, at the neuromuscular junction [44,2]. As such, they would be the first laminins that could be involved in formation or stabilization of synapses within the central nervous system.

There is now an abundance of different laminin chains, and the possibility of yet more to be discovered. Of these, at least six are expressed in various parts of the adult and developing retina (α2 [32]; α3 and 4 (see Results); β1 [30]; β1 and γ1 [31]; β2 [18,33,45]; γ3 (see Results)). By extension, we believe that laminins may be ubiquitous throughout the vertebrate nervous system. In this regard, it will be important to define all the laminin trimers that are associated with the nervous system, and the functions they may subserve in the developing and adult brain.

Laminin 5

The spatial and temporal expression of the eleven known laminin chains in development was studied. Laminin chain expression was determined using indirect immunohistochemistry. Temporally, laminin chains were expressed as early as embryonic day 16 (E16). Laminin β3 and γ2 were only expressed from E16 through P10 and not in P15 or in the adult. Spatially, the laminin chains of laminin-1 (α1/β1/γ1) were only expressed in the retinal vasculature. The component chains of laminin-5 (α3/β3/γ2) were expressed in the developing interphotoreceptor matrix (IPM). Laminin-13 (α3/β2/γ3) and laminin-14 (α4/β2/γ3) chains were expressed in the developing IPM and outer plexiform layer (OPL). Finally, laminin α5 was expressed in Bruch's membrane.

These appearance of the β and γ chains of laminin-5 only in the early developmental stages, suggest that they are important in retinal development up until the time of rod photoreceptor maturation. The presence of the component chains from laminin-13 and laminin-14 throughout development and adulthood provides evidence that these laminin heterotrimers have a variety of functions in the retina.

Developing Retina

The retina is formed from the optic vesicle, an outpocketing of the neural tube, which will eventually form the optic cup. The outermost layer will form the RPE while the innermost layer will thicken to form the neural retina (Zhao et al., 1995). Between this outer and inner layer is the subretinal space, which early in development is still continuous with the ventricular cavities of the brain. Adjacent to the subretinal space is the area where cells undergo cell division in the developing retina. Additionally, as the development of the retina continues, the subretinal space will shrink and fill with the outer segments of the photoreceptor and RPE cell processes (Libby, 1997b). This area of the subretinal space will be important to examine due to the important role it plays in retinal development. It will be important to closely examine the subretinal space as it shrinks and look at the extracellular components which are involved in this process.

The uniform epithelial sheet from which the retina arises is mitotically active. These mitotically active cells are known as retinal progenitor cells and make contact at the ELM and the ILM. When the progenitor cells divide, they lose contact with the ILM and move towards the ELM to undergo cell division (Hinds and Hinds, 1974). Birthdating studies have shown that although a pattern in the generation of cell types exists, several cell types can be generated simultaneously during development. In many species, it has been shown that ganglion cells are born first. However, it is also possible for second order cells such as horizontal or amacrine cells to be born around but not before ganglion cells. Many of these birthdating studies have shown that the retinal progenitor cell is multipotent up until the last cell division (Cepko et al, 1996). The multipotentcy of the retinal progenitor cell and the ability for more than one cell type to be born at once provides support for the role of extrinsic factors in retinal development.

In general, in the rat retina, the inner neurons of the neural retina are born during the embryonic stage while the outer neurons are born during the postnatal stage. At birth the RPE is well developed along with the ganglion cell layer and the inner nuclear layer, containing horizontal and amacrine cells (Hinds and Hinds, 1974; Hinds and Hinds, 1978; Hinds and Hinds, 1979; Hinds and Hinds, 1983). Additionally, the exterior limiting membrane is visible, although only bordered by the photoreceptors. In the following postnatal days, Müller cells will be born along with bipolar cells. Unlike the other neurons, rod photoreceptors are not born specifically before or after the day of birth. Rather, rods are usually born between embryonic day sixteen and postnatal day seven and eight. Around postnatal day three and five, the beginnings of the inner and outer segments become visible. It is not until approximately postnatal day eight to ten that the we see well developed inner and outer segments (Weidman and Kuwabara, 1968; Weidman and Kuwabara, 1969).

Animal Handling/Tissue Preparation

Animals were handled in accordance with the ARVO statement for the Use of Animals in Ophthalmic and Vision Science. Embryonic, postnatal, and adult retinas were obtained from Sprague-Dawley rats (Taconic; Germantown, NY). Timed pregnant rats, determined by Taconic as the first sperm positive day, were sacrificed by exposure to $CO_2$. Uteri were removed within five minutes of the cessation of breathing and placed on ice cold PBS, the embryos were dissected from the uteri and kept on ice. Whole heads of the embryonic day 16 rats were frozen and embedded (see below). Postnatal rats were scarified by exposure to $CO_2$ and their eyes were removed immediately. Whole eyes of postnatal day zero, three, and five rats were frozen and embedded (see below). The anterior chamber and lens of postnatal day eight, ten, and fifteen rats were removed. The resultant eyecup was embedded and frozen (see below).

Tissue (whole head, whole eye, and eyecups) were embedded as follows: washed in PBS, embedded in O.C.T. Compound (Miles Inc. Elkhart, Ind.), and rapidly frozen by immersion in either isopentane cooled in liquid nitrogen or in ethanol cooled in dry ice. Before cutting, blocks were stored at −20° C.

Transverse sections at 10 µm were cut on a Leica cryostat. Sections were placed on Superfrost/Plus Microscope Slides (Fisher Scientific, Pittsburgh, Pa.). Cut sections were stored at −20° C. until use.

Immunostaining

Immunohistochemistry was performed by washing sections in phosphate buffered saline (PBS: 137mM NaCl, 2.68 mM KCl, 10 mM $Na_2HPO_4$, 1.76 mM $KH_2PO_4$, pH 7.35) for three washes of five minutes each. Using a PAP pen (Polysciences Inc. Warrington, Pa.), sections were separated to prevent the mixing of antibodies. Approximately 30 μl of the primary antibodies were placed on each section. Slides were placed in a humidified chamber for ninety minutes at room temperature or overnight at 4° C. Unbound antibodies were removed by two 10 minute washed in PBS. Approximately 35 μl of secondary antibody was placed on each section. Slides were placed in a humidified chamber for one hour at room temperature. Unbound secondary antibodies were removed by two 10 minute washed in PBS. Slides were coverslipped in Prolong Antifade (Molecular Probes; Eugene, Oreg.) to reduce photobleaching.

The embryonic day 16 (E16) and postnatal day 5 (β5) slides were viewed on a Leica Confocal Lasar Scanning Microscope (Leica NTS 4D) at the Cutaneous Biology Research Center of Harvard Medical School. Images were exported from the CLSM software (Leica NS Version 11.2) into Adobe photoshop (version 4). The P0, P3, P8, P10, P15, and adult slides were viewed on a conventional light microscope. Images were taken on the light microscope and scanned into Adobe photoshop (version 4).

Antibodies

The antibodies used were: laminin-1 (12116-018, Life Technologies; rabbit polyclonal); laminin-5 (4101, gift of R. E. Burgeson; rabbit polyclonal); laminin α2 (12067-014, Life Technologies; mouse monoclonal); laminin α3 (BM-2, gift of R. E. Burgeson; mouse monoclonal); laminin α4 (Miner et al., 1997; rabbit polyclonal); laminin α5 (Miner et al., 1997; rabbit polyclonal); laminin β1 (C-21, Sanes and Chiu, 1983; mouse monoclonal); laminin P2 (Sanes et al., 1990); guinea pig polyclonal; Sanes and Chiu, 1983; mouse monoclonal); laminin β3 (6F12, Rousselle et al., 1991; mouse monoclonal); laminin γ1 (D-18, Sanes et al., 1990; mouse monoclonal); laminin γ2 (Sugiyama et al., 1995; rabbit polyclonal); laminin γ3 (R-18, gift of M. F. Champliaud; rabbit polyclonal). Primary antibodies were diluted in PBS containing 2% goat serum, 0.1% triton, and 0.05% Na azide. Secondary antibodies were diluted in PBS containing 2% goat serum and 0.05% Na azide.

Embryonic Day 16

Embryonic day 16 (E16) is an important developmental stage to examine in the rat retina because it is the first day of rod genesis. At this time, the subretinal space begins to shrink bringing the RPE and neuroepithelium close together. Furthermore, it is possible to see well differentiated ganglion cells on the vitreal side of the neuroepithelium. In the E16 rat retina, the three chains associated with laminin-1 (α1, β1, γ1) were examined using a polyclonal antibody. This antibody does not react with any area of the neuroepithelium, rather it is only seen in the vasculature. A monoclonal antibody against laminin α2 yielded similar results to those for laminin-1, staining was only in the vasculature basement membrane and not in the neuroepithelium. Immunoreactivity against both the laminin α3 and α4 chains was seen on the apical surface of the neuroepithelium in the subretinal space. Laminin α5, much like α1 and α2 is only associated with the retinal vasculature. Laminin α5 immunoreactivity is particularly prominent on the ventricular side of the RPE, which is the basement membrane also known as Bruch's membrane.

As noted earlier, laminin β1 immunoreactivity is only associated with the retinal vasculature. In addition to using a polyclonal antibody against laminin-1, a monoclonal antibody directed against β1 yielded similar results. Immunoreactivity against laminin β2 is seen in both the RPE and the neuroepithelium. In the RPE, β2 is associated with both the apical and basal sides. Additionally, β2 is seen on the vitreal surface of the neuroepithelium. Laminin β3 immunoreactivity is present on the apical surface of the neuroepithelium and appears to be filling the subretinal space, similar to the reactivity seen in this area with β2. This immunoreactivity of β3 in the subretinal space is different than in the adult retina, which contains no β3 immunoreactivity. Thus, the appearance of β3 is limited to a short period in retinal development.

As stated above, laminin γ1 is only seen in the retinal vasculature and not in the neuroepithelium. As with β1, a monoclonal antibody against γ1 was used in addition to the laminin-1 polyclonal antibody to confirm the earlier results. In the neuroepithelium, laminin β2 is seen on the apical surface. As with β3, the immunoreactivity of γ2 in the developing retina is a novel finding, one that has not previously been reported in the adult, and appears to be limited to a short developmental time period. The laminin γ3 chain is also present in the developing retina. γ3 immunoreactivity appears on apical surface of the neuroepithelium.

Postnatal Day 0

Rod genesis peaks around the day of birth in rodents, thereafter, the first opsin photopigments are detected (Carter, Dawson and LaVail, 1979; Hicks and Barnstable, 1987). By this time, the RPE cells have become a single layer of squamous-like cells (Libby et al, 1997b) and the subrentinal space has continued to shrink. Laminin α1 and α2 in the P0 rat continue to be associated with the retinal vasculature. Laminin α3 and α4 immunoreactivity is apparent on the apical surface of the retina filling the subretinal space. The basement membrane of the RPE, Bruch's membrane, continues to be immunoreactive with laminin α5.

As with the results seen in the E16 rat retina, laminin β1 labels only the retinal vasculature. In the RPE, laminin β2 is associated with both the basal and apical sides while also continuing to fill the subretinal space. Additionally, β2 is reactive with the vitreal side of the neuroepithelium. The immunoreactivity of laminin β3 continues to be present in the subretinal space, as seen in the results from E16.

The retinal vasculature is seen to be reactive with laminin γ1, as similarly seen with α1 and β1. Laminin γ2 immunoreactivity continues to be associated with the diminishing subretinal space, as does laminin γ3. Furthermore, γ3 is seen distributed on the vitreal side of the neuroepithelium.

Postnatal Day 3

Around P3, rod morphogenesis is apparent with rod inner segments beginning to protrude into the subretinal space (Galbavy and Olson, 1979). In the RPE, Bruch's membrane is well delineated on the basal side of the RPE. At this age, laminin α1 and α2 are not associated with the RPE or neuroepithelium, but rather only in the retinal vasculature. The immunoreactivity of laminin α3 is now seen on both the apical and vitreal sides of the neuroepithelium. On the apical side, α3 appears to be in the subretinal space. The immunoreactivity of α3 on the vitreal side is weak and diffuse. Immunoreactivity of laminin α4 is similar to that of α3 in that it is seen on the apical and vitreal sides of the neuroepithelium. Laminin α5 is seen only in the retinal vasculature, much like α1 and α2. Laminin α5 is reactive in Bruch's membrane, seen as a straight line running across the basal side of the RPE.

The RPE and neuroepithelium do not show any reactivity with laminin β1. As with its laminin-1 partner, β1 reactivity is only seen in the retinal vasculature. Laminin β2 immunoreactivity fills the subretinal space between the apical surfaces of the RPE and neuroepithelium. Immunoreactivity is also seen on the vitreal side of the neuroepithelium. As with β2, laminin β3 reactivity fills the subretinal space. However, β3 staining is restricted to this area and is not seen on the vitreal surface of the neuroepithelium.

As seen in the α and β chains of laminin-1, laminin γ1 is only seen in the retinal vasculature. Immunoreactivity of laminin γ2 is seen in the subretinal space. The presence of γ2 reactivity in the neuroepithelium is consistent with the results from β3 and with the results from previous developmental stages. Laminin γ3 reactivity continues to be associated with the subretinal space and the vitreal side of the neuroepithelium.

Postnatal Day 5

By P5, the outer segment have begun to form and the OPL begins to appear (Weidman and Kuwabara, 1968). Now that the outer segments are developing and protruding into the subretinal space, this area will be referred as the interphotoreceptor matrix (IPM). Laminin α1 and α2 reactivity appear only in the retinal vasculature. Laminin α3 immunoreactivity is seen throughout the IPM. Additionally, α3 is seen associated with the outer plexiform layer. Laminin α4 continues to react with the IPM; and as with alpha3, it appears to be associated with the OPL. As in P3, reactivity of laminin α5 is seen in the well delineated Bruch's membrane.

As seen in all the earlier developmental stages examined, laminin β1 reactivity is only associated with the retinal vasculature. Immunoreactivity from laminin β2 is seen diffusely throughout the IPM and some staining is seen on the apical side of the RPE. Laminin β3 immunoreactivity appears to be confined to the IPM and not associated with vitreal areas of the neural retina.

Immunoreactivity of laminin γ1 continues to appear only in the retinal vasculature. Laminin γ2, similar to β3, is only associated with the IPM. Laminin γ3 is also seen in the IPM; however, it is additionally seen in the OPL.

Postnatal Day 8

By P8, the inner segments of the rod photoreceptors are well developed. Additionally, the outer plexiform layer (OPL) is well formed by this stage (Weidman and Kuwabara, 1969). Antibodies against laminin α1 and α2 continue to be reactive with the retinal vasculature and absent in the RPE and neural retina. Immunoreactivity from laminin α3 is seen in both the IPM and the OPL Laminin α4 is apparent in the IPM, the OPL, the and IPL. These observations are consistent with the results of α4 immunoreactivity in the adult rat retina (Libby, 1997). Furthermore, α4 reactivity is seen in Bruch's membrane, this result was not seen in earlier stages. Antibodies against laminin α5 continue to stain Bruch's membrane as in earlier developmental stages.

Immunoreactivity from laminin β1 continues to be seen in the retinal vasculature. Laminin β2 reactivity is present in the IPM and appears to be surrounding the outer segments of the rod photoreceptors. Diffuse β2 reactivity continues to be seen on the apical side of the RPE and in the OPL. Laminin β3 immunoreactivity is apparent throughout the IPM. The β3 immunoreactivity is distinctly weaker in the P8 developmental stage than in the previous stages examined.

As seen with α1 and β1, laminin γ1 reactivity is only seen in the retinal vasculature. Immunoreactivity from laminin γ2 appears in the IPM and seems to be restricted to this region. As with the results from β3, the immunoreactivity from antibodies against γ2 appears to be weaker than in previous stages. Laminin γ3 reactivity is seen in the IPM and appears to be surrounding the outer segments of the rod photoreceptors. Furthermore, γ3 reactivity is apparent in the OPL.

Postnatal Day 10

By P10, the IPL is more compact and the outer segments are clearly protruding into the subretinal space. Additionally, Müller cells can be seen throughout the neural retina. As seen in earlier developmental stages, laminin α1 and α2 reactivity is only present in the retinal vasculature. Laminin α3 immunoreactivity is apparent in the IPM and diffusely in the OPL. Immunoreactivity from laminin α4 is present in the IPM, surrounding the outer segments of photoreceptors, and in the OPL and the IPL. Immunoreactive staining in Bruch's membrane is not as apparent in P10 as it was in P8. However, reactivity from laminin α5 is expressed in Bruch's membrane.

The laminin β1 staining continues to only be associated with the retinal vasculature. Laminin β2 immunoreactivity is present throughout the IPM, surrounding the inner and outer segments. Additionally, diffuse staining is seen in the OPL. Immunoreactivity from laminin β3 continues to be seen in the IPM. The reactivity of β3 continues to appear weaker than in earlier stages.

As seen in earlier developmental stages, laminin γ1 reactivity appears only in the retinal vasculature in the P10 stage. Weak laminin γ2 immunofluorescence is apparent in the IPM. Laminin γ3 reactivity is present in the IPM around the inner and outer segments. Further reactivity is seen in the OPL.

The distinctly weaker reactivity seen from β3 and γ2 in the P8 and P10 developmental stages suggests that the β and γ components of laminin-5 are turning off.

Postnatal Day 15

By P15, development of the retina is nearly complete. The three cellular and two synaptic layers in the neural retina are recognizable and electroretinographic responses are present (Weidman and Kuwabara, 1968). Laminin α1 and α2 reactivity is only detected in the retinal vasculature (not shown). Laminin α3 immunofluorescence continues to be present in the IPM and diffusely in the OPL. α3 reactivity is also present at this stage in the exterior limiting membrane (ELM, not shown). Laminin α4 immunoreactivity is seen in the IPM, the OPL, and the IPL. Additionally, immunoreactivity of α4 is seen in radial fibers, presumed to be Müller cells. Bruch's membrane continues to be stained by laminin α5.

As with α1, laminin β1 reactivity is seen in the retinal vasculature and not in the neural retina. Laminin β2 immunofluorescence is clearly seen surrounding the inner and outer segments in the IPM and additionally in the OPL. Unlike previous developmental stages, laminin β3 immunoreactivity is not detected in the IPM. β3 reactivity is not seen in any areas of the neural retina or RPE.

Much like the observations with α1 and β1, laminin γ1 reactivity is only detected in the retinal vasculature. Immunoreactivity from laminin γ2 is no longer seen throughout the IPM as in earlier stages. Furthermore, no γ2 reactivity is seen in the neural retina. Laminin γ3 immunofluorescence continues to be present in the IPM along with the OPL. Additional reactivity from γ3 is seen diffusely in the ELM.

Adult

Adult rat retinas were examined in order to detect any changes in laminin expression between late developmental stages and adulthood. Results from immunohistochemistry in the adult rat are not shown here. Together, Dr. Richard Libby and I characterized the laminin chains in the adult retina. The results presented here are consisitant with those from our earlier experiments. As seen throughout all the developmental stages examined, laminin α1 and α2 are only reactive with the retinal vasculature. Laminin α3 immunofluorescence continues to be seen in the IPM and in the OPL. As seen in the P15 stage, α3 reactivity is present where Müller cell processes form the ELM. As observed in the later developmental stages, laminin α4 reactivity is widely distributed throughout the retina. α4 reactivity is detected throughout the IPM and in the OPL and the IPL as well. As seen in the P10 and P15 stages, α4 continues to be associated with radial fiber, presumed to be Müller cells. Laminin α5 immunoreactivity is not associated with the neural retina and continues to be seen in Bruch's membrane.

As seen in all the developmental stages, reactivity from laminin β1 is only associated with the retinal vasculature. Laminin β2 immunoreactivity has been reported in earlier studies to be present in the IPM (Hunter et al., 1992; Libby et al., 1997a). Results from adult rat retinas used in these experiments are consistent with earlier data. Additional reactivity from β2 is present in the OPL. Laminin β3 reactivity is not detected in the adult retina. These results are similar to those seen in the P15 retina.

The reactivity of laminin γ1 in the adult retina is constant with the results from the previous developmental stages, γ1 is only detected in the retinal vasculature. Immunoreactivity from laminin γ2, similar to the results in the P15 stage, is not present in the neural retina or the retinal vasculature of the adult rat. Laminin γ3 immunoreactivity is prominent in the IPM surrounding the inner and outer segments. Additional γ3 reactivity is associated with the ELM and the OPL.

Overview

Laminins are involved in numerous processes such as cell migration, cell differentiation, and cell adhesion. In the retina, close adhesion between the RPE and neural retina is important to photoreceptor function. The role of laminins in retinal adhesion is enhanced by the presence of integrins in the retina. The adhesive properties of laminins may be mediated in part, by retinal integrins. One such integrin heterodimer is α6/β1.

We have examined the laminin chains and others throughout development to see what developmental changes are occurring and to provide more insight into their roles in the retina.

We have shown that there are considerable changes occurring in laminin chain expression throughout development. Early in development, the component chains of laminins-5, laminin-13, and laminin-14 are expressed in the neural retina. In the later developmental stages, specifically after rod genesis is complete, the β and γ chains of laminin-5 are turned off, leaving only laminin-13 (α3/β2/γ3) and laminin-14 (α4/β2/γ3) expressed in retina.

Laminin-5 Chains

A significant developmental change in laminin expression is seen with the β and γ chains of laminin-5 (α3/β3/γ2). The β and γ chains of laminin-5 are apparent in the subretinal space of the neural retina as early as E16, but not in the adult. β3 and γ2 immunoreactivity is present through P10, although as early as P8 the intensity of the immunoreactivity is diminishing, and immunoreactivity completely disappears by P15.

Although the components of laminin-5 have not been examined in the developing rat nervous system, the chains have been examined in the developing mouse (Aberdam et al., 1994b; reviewed in Ryan et al., 1996). In these studies, the 3 and γ2 chains were reported to be present in the developing choroid plexus as early as embryonic day 16. Additionally, all three chains of laminin-5 (α3/β3/γ2) were reported in cerebrospinal fluid at the same developmental stage (Aberdam et al., 1994b).

In examining the spatial expression of the laminin-5 chains immunoreactivity in the stages of retinal development, we believe that these chains are important in the adhesion between RPE and neuroepithelium. As the retina develops, the subretinal space begins to shrink, bringing the RPE and neuroepithelium closer together. During this time, the three chains of laminin-5 are present in the subretinal space. As the retina continues to differentiate and the outer segment are elaborated from the apical surface to the photoreceptor cell layer (ONL), the matrix between the adjacent photoreceptors matures into the IPM. During this maturation the apparent intensity of the immunoreactive signal for both β3 and γ2 laminin become weaker. At P15, when the development of the retina is nearly complete, β3 and γ2 laminin chains are undetectable by immunocytochemical techniques. This apparent turning off of β3 and γ2 shows that their presence in the subretinal space is necessary up until photoreceptor maturation is complete. Unlike either β3 and γ2, laminin α3 continues to be expressed by the neural retina into adulthood. However, α3 is likely to be associated with other laminin chains, namely β2 and γ3, which are known to be expressed by the neural retina.

We have also examined laminin 13 and 14 chains throughout retinal development. Immunoreactivity from these chains is present throughout retinal development. Before the neuroepithelium differentiates, α3 and α4, β2 and γ3 immunoreactivity is only present in subretinal space. As the of the neuroepithelium differentiates, immunoreactivity from these chains is seen in the OPL. Furthermore, α4 immunoreactivity is seen in the IPL and in radial fibers believed to be Müller cells. The chains of laminin-13 and laminin-14 are important components in the adhesion between the RPE and developing neuroepithelium.

Laminin β2-Deficient Mice

We have characterized disruptions in the central nervous system of these laminin β2-deficient animals through the fourth postnatal week.

Experimental Procedures

Animals

Mice heterozygous for a null mutation in the laminin β2 gene (Noakes et al., 1995a) were a gift of Joshua Sanes (Washington University, Saint Louis, Mo.). These mice were created by a homologous recombination that targeted the second exon of the mouse laminin β2 gene. DNA transfer blot analysis has confirmed the presence of a disrupted laminin β2 gene; protein transfer blot analysis has confirmed the absence of laminin β2 protein in homozygous nulls (Noakes et al., 1995a). Heterozygous animals, maintained in a 12-hour day/night cycle, were bred in our colony at Boston College. The day of birth was defined as postnatal day (P) 0. Genotypes of the offspring of heterozygous matings were determined as previously described (Noakes et al., 1995a).

In all respects, heterozygous animals appear indistinguishable from homozygous normal mice. Thus, heterozygous (+/−) and homozygous (+/+) animals, both of which are phenotypically wild-type, were used as controls.

Immunohistochemistry and Histology

A mouse monoclonal antibody that recognizes rhodopsin (Ret-P1; Fekete and Barnstable, 1983) was a gift of C. Barnstable, Yale University. Antibodies that recognize laminins were obtained as follows: a polyclonal anti-laminin-1 (recognizes laminins α1, β1, and γ1), from Life Technologies, Bethesda, Md.; a polyclonal anti-laminin α4, from J. R. Sanes, Washington University. A mouse monoclonal antibody that recognizes synaptic ribbons was raised in our laboratories (B16; Balkema, 1991; Balkema and Rizkalla, 1996). A mouse monoclonal antibody that recognizes synaptophysin was obtained commercially (Boehringer Mannheim, Indianapolis, Ind.). Secondary antibodies were obtained from Sigma (Saint Louis, Mo.) and Incstar (Stillwater, Minn.).

Unfixed tissue was prepared, embedded, and frozen as described previously (Libby et al., 1996). For preparation of paraformaldehyde-fixed tissue, eyes were removed and a hole was made at the ora serrata using a hypodermic needle. The tissue was then placed in ice-cold 4% paraformaldehyde in phosphate-buffered saline (PBS; 137 mM NaCl, 2.68 mM KCl, 10 mM $Na_2HPO_4$, 1.76 mM $KH_2PO_4$, pH 7.4). After approximately 30 minutes, the anterior chamber and lens were removed from the eye and the resultant eyecup was fixed again for 2 hours or overnight. Following fixation, the tissue was placed into an ascending series of sucrose solutions (5%, 10%, 15%, 20% in PBS), incubated overnight at 4° C. in a mixture of 20% sucrose and 80% OCT (Miles, Elkhart, Ind.), then changed to a fresh solution of 20% sucrose and 80% OCT. The tissue was then frozen and cut at 10 μm, as previously described (Libby et al., 1996). For some histological examinations, the tissue was fixed in 3% glutaraldehyde and 2% formaldehyde in PBS, then treated as described above. Immunohistochemistry on unfixed and paraformaldehyde-fixed tissue was performed as previously described (Libby et al., 1996; Libby et al., 1997).

Assay for Apoptotic Cell Death

For consistency, sections from P15 and P20 animals were chosen that included the optic nerve or were close to it. Apoptotically dying cells in these sections were detected using an in situ cell death detection kit (Boehringer Mannheim, Indianapolis, Ind.). This kit detects dying cells by the Terminal deoxynucleotidyl transferase-mediated dUTP Nick End Labeling (TUNEL) method (Gavrieli et al., 1992), which labels the ends of fragmented DNA with labeled UTP (here, the UTP is coupled to fluorescein), using the enzyme terminal deoxynucleotidyl transferase. Paraformaldehyde-fixed sections (10 μm; see above) were prepared for labeling by fixation onto slides with 4% paraformaldehyde in PBS for 20 minutes at room temperature, then were permeabilized and labeled according to the manufacturer's instructions. Following labeling, sections were mounted in a glycerol-based solution containing paraphenylenediamine (1 mg/ml) to reduce photobleaching.

Electroretinography

Electroretinograms (ERGs) were performed on animals on or near the twentieth postnatal day. All preparative procedures were performed in normal room light. Animals were anesthetized with Tractane (approximately 12.5 mg/kg), followed by Nembutal (approximately 65 mg/kg), then placed into a stereotactic holder. A reference electrode, made from silver wire, was placed between the skin and the skull near the bregma and secured with cynoacrylate. After suturing the eye open, a drop of atropine (0.54 mg/ml) was placed onto the eye for approximately 1 minute. The animal was then placed into a light-tight Faraday cage. After aligning the animal with the light source, a cotton wick electrode coupled to a silver-silver chloride half cell was placed onto the animal's cornea in a position that did not attenuate the light flashes. A test flash was presented to the animal to check for proper electrode placement. Following a 21-minute dark-adaptation, animals were presented 10 separate 50 ms flashes that were separated by 2 seconds (PS22 Photopic stimulator, Grass Instruments); the responses were amplified using a Dam 50 Differential Amplifier (World Precision Instruments), and recorded and averaged using a MacLab 4S (AdInstruments). For each animal, at least one set of recordings was made over a 4.2-log range of intensities, starting with least bright. A 21-minute period of dark-adaptation preceded any subsequent recording sessions.

Histoloqy

During the first ten or eleven postnatal days, retinae from laminin β2-deficient and control mice were not grossly different. By P13, however, the first differences between the laminin β2-deficient and control mice become evident; in particular, the thickness of the retinae in laminin β2-deficient mice is markedly reduced by P15. This reduction is due almost entirely to a decrease in photoreceptor length: although nuclear and plexiform (synaptic) layers in laminin β2-deficient retinae appear largely normal (as judged by width), the photoreceptor outer segments, and possibly inner segments, are clearly shorter. The period during which this difference becomes apparent is the period when outer segments are undergoing their maximal lengthening (the beginning of the third postnatal week; LaVail, 1973).

In wild-type (+/?) mice, outer and inner segments reach their maximum length over the subsequent two postnatal weeks. In contrast, in laminin β2-deficient mice, outer and inner segments fail to increase dramatically over this same time period. At P25 in wild-type (+/?) mice, photoreceptor outer and inner segment lengths (approximately 32 and 16 μm, respectively) have reached the normal range for adult mice (LaVail, 1973); in contrast, inner and outer segments in retinae from laminin β2-deficient mice are approximately 50% shorter. Thus, by the fourth postnatal week (that is, at their maximal survival time), laminin β2-deficient mice have severely retarded development of outer and inner segments, or a disposition to shorter outer and inner segments, presumably as a consequence of the laminin β2 deficiency.

Although the morphology of the photoreceptors is clearly altered in laminin β2-deficient mice, these mice still express the photopigment, rhodopsin, in their outer segments. An antibody to rhodopsin (Ret-P1, Barnstable, 1980; Fekete and Barnstable, 1983) reveals rhodopsin in laminin β2-deficient mice that is properly localized to the outer segments. Although immunohistochemistry cannot determine whether laminin β2-deficient mice produce wild-type (+/?) amounts of rhodopsin, we predict that, judging by the production and location of photopigment, these photoreceptors would be capable of responding to light.

In a screen of laminin β2-deficient retinae, we did not detect any marked disruptions in several other cell types, including bipolar cells (using an antibody against protein kinase C), horizontal cells (using an antibody against calbindin), and Müller cells (using an antibody to vimentin). These data, when coupled with the mostly normal anatomy of the retinae from laminin β2-deficient mice (see above), show that only photoreceptor development is altered by the removal of laminin β2.

Apoptosis

In the mouse retina, the number of cells undergoing cell death generally follows a Gaussian distribution, beginning prior to birth, peaking around P9, and ceasing around P25. Also, within this distribution, inner retinal cells (i.e. ganglion cells and amacrine cells) die earlier than outer cells (i.e. photoreceptors and bipolar cells). To test whether the laminin β2-deficient mice were undergoing these normal developmental processes, we assayed for programmed cell death on two different days, P15 and P20.

At P15, in the normal mouse retina, cell death is primarily restricted to rod photoreceptors and rod bipolar cell populations (Young, 1984). In wild-type mice, the type (based on location) and number of cells undergoing programmed cell death (Table One) is consistent with previous reports (Young et al., 1984). Laminin β2-deficient mice had approximately twice the amount of programmed cell death (Table one).

TABLE 1

| Age | Phenotype | #sections | #retinae | #apoptotic cells (per section) |
|---|---|---|---|---|
| P15 | | | | |
| | wild-type | 8 | 3 | 16.5 ± 1.5 |
| | β2-deficient | 7 | 2 | 35.7 ± 6.1 |
| P20 | | | | |
| | wild-type | 8 | 3 | 3.6 ± 1.2 |
| | β2-deficient | 7 | 2 | 9.3 ± 2.2 |

Sections from P15 and P20 animals were chosen that included the optic nerve or were close to it. Raw numbers were averaged and are presented as means ± standard errors of the mean (SEM).

In normal mouse development, by the twentieth-postnatal day the number of cells undergoing cell death declines rapidly and is limited mainly to photoreceptors. At P20, wild-type retinae contained fewer apoptotic cells than at P15; laminin β2-deficient mice also have a decrease in apoptotic cells at P20 (Table One).

Therefore, laminin β2-deficient mice do have elevated programmed cell death; however, they are still following the basic developmental trend: a decrease in dying cells with age. Moreover, the rate of decrease in cell death is parallel to that of the rate in the littermate controls, showing that cell death in the laminin β2-deficient mice is slowing as it should. In addition, the increase in dying cells in the laminin β2-deficient mice is relatively small in number when compared to the total number of retinal cells, so that there is little or no effect on retinal function merely due to a paucity of cells.

It should also be noted that at both ages examined there is no apparent clumping of apoptotic cells that would be suggestive of necrosis (Vaux, 1993): apoptotic cells are generally surrounded by viable cells. This suggests that the retina of the laminin β2-deficient mouse is not significantly affected by the other pathologies (e.g., kidney disturbances) occurring in the animal.

Laminins in the IPM of Laminin D2-deficient Mice

We have examined the retinae of wild-type and laminin β2-deficient animals for the presence of the other components of laminins 12 (α3β2γ3) and 13 (α4β2γ3) ; i.e., laminins α3, α4, and γ3. We examined the expression of RNAs encoding these three chains (by in situ hybridization). We have not detected any obvious changes in expression of RNA encoding these chains, showing that there are no gross changes in transcription of these chains as a result of the removal of laminin β2 protein.

We have been able to examine the protein expression of two of the three components. Laminins α4 and γ3 are present in the retinae of wild-type mice. In all three species, these laminin chains are present in three distinct locations: (1) the interphotoreceptor matrix; (2) the outer plexiform layer; and (3) to varying degrees, the inner plexiform layer. Although laminin β2 protein is, by definition, absent from laminin β2-deficient retinae, we cannot detect any gross disturbances in the distribution of its presumed partners, laminins α4 and γ3, in the laminin β2-deficient retinae in any of these locations. These data are consistent with the apparent lack of change in expression of RNA encoding these chains, and suggest that the loss of laminin β2 protein does not result in a gross change in the deposition of laminins α4 and γ3.

Notably, in the absence of laminin β2, laminins α4 and γ3 continue to be expressed in the IPM, wherein they are almost certainly extracellular. These data show that there is a compensatory expression of another, perhaps unknown, laminin β chain. We examined the distribution of laminin β1 in the retina of these animals, to ascertain whether it could substitute for laminin β2 in retinal laminin trimers containing the α4 and γ3 chains. Using a polyclonal antiserum that reacts with all three chains of laminin-1 (α1, β1, and γ1), we can only detect the laminin chains that are associated with the retinal vasculature: we found no ectopic laminin β1 (nor laminin α1 and γ1) in the laminin β2-deficient retinae. We have no mouse-reactive anti-laminin β3 antibodies, leaving open the possibility that laminin β3, which is not normally associated with the adult neuronal retina, may substitute for laminin β2 in the laminin β2-deficient retinae. However, in situ hybridizations using probes that detect RNA encoding laminin β3 show that there are no alterations in expression of the RNA encoding this chain. It is therefore likely that a novel laminin β chain may substitute for laminin β2 in the interphotoreceptor matrix and outer plexiform layer of laminin β2-deficient mice.

Light Responses

An electroretinogram (ERG) documents the summed electrical activity of the retina, thereby yielding information about its overall physiology. In particular, an ERG can describe the response of photoreceptors and retinal interneurons independently to light: photoreceptor responses are present as an initial downward deflection, known as the a-wave (Dowling, 1960; Brown and Wiesel, 1961), whereas the transmission to the inner retinal interneurons is present as a subsequent upward deflection, known as the b-wave (Brown and Wiesel, 1961; Rager, 1979; Stockton and Slaughter, 1989). The amplitude of these waves, their shape, and the time it takes to reach a peak voltage ("time to peak", or "implicit time") can be used as diagnostic tools mine the physiological health of the retina.

We performed ERGs on wild-type (+/?) and laminin β2-deficient mice. At maximum stimulus intensity, the ERG of a wild-type (+/?) mouse is typical, characterized by an initial downward deflection caused by the electrical activity of the photoreceptor cells (the a-wave) which is then swamped out at approximately 50 ms by the field potential arising from the second order interneurons (the b-wave). The b-wave reaches its peak at approximately 100 ms, then the ERG falls quickly back to baseline, due to further processing by retinal interneurons.

The overall ERG of the laminin β2-deficient mouse is pathological. However, importantly, the a-wave appears normal, both in terms of its amplitude and the time to peak (Table Two).

TABLE 2

Electroretinogram responses for control and lamininβ2-deficient mice at maximal light intensity.

| Laminin β2-deficient mice | Age (P) | a-wave implicit time | $A_{max}$ | b-wave implicit time | $B_{max}$ | B/A ratio |
|---|---|---|---|---|---|---|
| | 18 | 46.5 | −900 | 97.0 | 1410 | 1.57 |
| | 20 | 38.5 | −740 | 93.0 | 1310 | 1.77 |
| | 20 | 46.5 | −510 | 115.5 | 910 | 1.78 |
| | 20 | 46.5 | −810 | 83.0 | 1690 | 2.09 |
| | 20 | 40.5 | −800 | 97.0 | 1590 | 1.99 |
| | 21 | 46.5 | −370 | 99.0 | 940 | 2.54 |
| | 21 | 46.5 | −760 | 107.0 | 1670 | 2.20 |
| Average | | 44.5 | −699 | 99 | 1360 | 1.99 |
| Normal | | | | | | |
| | 18 | 58.5 | −320 | 141.5 | 1221 | 3.82 |
| | 20 | 52.5 | −440 | 97.0 | 1980 | 4.50 |
| | 20 | 44.5 | −790 | 85.0 | 2410 | 3.05 |
| | 21 | 56.5 | −430 | 115.5 | 1520 | 3.53 |
| | 21 | 54.5 | −1110 | 113.5 | 3330 | 3.00 |
| | 21 | 52.5 | −1580 | 109.0 | 4810 | 3.04 |
| | 21 | 44.5 | −1770 | 87.0 | 5150 | 2.91 |
| | 22 | 38.5 | −400 | 70.5 | 1260 | 3.15 |
| | 22 | 44.5 | −840 | 83.0 | 2520 | 3.00 |
| Average | | 49.6 | −853.3 | 100.2 | 2689 | 3.15 |
| p value | | 0.092 | 0.941 | 0.875 | 0.035 | 0.00002 |

Comparing the ERG responses of laminin β2-deficient and normal mice at maximum light intensity clearly shows the disruption of the ERG caused by laminin β2 deficiency. Laminin β2 deficient mice have statistically similar (significance is defined as a p value <0.05; significant differences are bolded) A- and b-wave implicit times (time to peak) and a-wave amplitudes. The b-wave of the laminin β2 deficient mice is clearly attenuated; it is significantly smaller. The ability of the a-wave to elicit a b-wave (estimated by dividing the b-wave response by the a-wave response; the B/A ratio) is significantly lower in laminin β2-deficient mice).

This suggests that, although the morphology of the photoreceptor outer segments is clearly affected by the lack of laminin β2, the overall ability of the photoreceptors to respond to light is not.

In contrast, there is a marked disruption of the b-wave of ERGs from laminin β2-deficient animals. The b-waves have normal implicit times, but their amplitudes are significantly reduced (Table Two). Moreover, the ERG does not return to baseline as in the normal mouse; rather, it generally remains well above baseline for over a second. In fact, at the time of the subsequent stimulation (2 seconds after the first), the physiology of the retina is still disturbed: in general, the laminin β2-deficient retinae demonstrate ERGs that are at a negative potential at the time of the next stimulation.

Photoreceptors, and thereby the retina, respond to increasing light levels with increasing electrical activity up to the point at which they reach a saturated, maximal response. Wild-type (+/?) mice exhibit the normal response of the retina to increases in light intensity: (1) at low light levels, the b-wave is the only electrical activity observable in the ERG; as the light intensity increases, its amplitude and implicit times increase; (2) a-waves are first detectable at higher light levels than b-waves; like a-waves, their amplitudes and implicit times increase with increasing light intensity.

The response of laminin β2-deficient retinae to increases in light intensity is fundamentally normal: both the a- and b-waves increase with increasing light intensity. However, at maximal intensities, although the a-waves of the laminin β2-deficient retinae are similar to those of normal controls, the b-waves are greatly attenuated. A summary of data obtained from several animals clearly shows that the laminin β2-deficient retinae exhibit near-normal a-waves, but b-waves that are attenuated at all light intensities tested. The net result is that, on average, the b- to a-wave ratios are significantly lower in the laminin β2-deficient mice (1.99 vs. 3.15; Table Two). Together, these data show that the laminin β2-deficient retinae are capable of detecting light nearly normally, but that information transfer from photoreceptors to second order cells (the retinal interneurons) is compromised.

The apparent failure of transmission can be a disruption of the synaptic layer in which photoreceptors contact second-order neurons, the outer plexiform layer. Indeed, the outer plexiform layer of laminin β2-deficient mice appears not to contain the wild-type number of rod synapses: an antibody specific for photoreceptor "ribbon" synapses (B16; Balkema, 1991; Balkema and Rizkalla, 1996) demonstrates fewer photoreceptor synapses in the outer plexiform layer of the laminin β2-deficient mice. This disruption of the outer plexiform layer likely accounts for the lack of a normal b-wave, in the presence of a normal a-wave, in the laminin β2-deficient mice.

Literature Cited Under the Section of "Laminins 13 and 14"

[1] Timpl R. Macromolecular organization of basement membranes. Curr Opin Cell Biol 1996;8:618–624.

[2] Miner J H, Patton B L, Lentz S I, Gilbert D J, Snider W D, Jenkins N A, Copeland N G, Sanes J R The laminin alpha chains: expression, developmental transitions, and chromosomal locations of α1–5, identification of heterotrimeric laminins 8–11, and cloning of a novel α3 isoform. J Cell Biol 1997;137:685–701.

[15] De Arcangelis A, Neuville P, Boukamel R, Lefebvre O, Kedinger M, Simon Assmann P. Inhibition of laminin α1-chain expression leads to alteration of basement membrane assembly and cell differentiation. J Cell Biol 1996;133:417–430.

[17] Liesi P. Laminin-immunoreactive glia distinguish regenerative adult CNS systems from non-regenerative ones. EMBO J. 1985b;4:2505–2511.

[18] Hunter D D, Murphy M D, Olsson C V, Brunken W J. S-laminin expression in adult and developing retinae: a potential cue for photoreceptor morphogenesis. Neuron 1992b;8:399–413.

[19] Hunter D D, Brunken W J; β2 laminins modulate neuronal phenotype in the rat retina. Mol Cell Neurosci 1997;10:7–15.

[24] Hunter D D, Llinas R, Ard M, Merlie J P, Sanes J R. Expression of s-laminin and laminin in the developing rat central nervous system. J Comp Neurol 1992a;323:238–251.

[30] Sarthy V. Collagen IV mRNA expression during development of the mouse retina: an in situ hybridization study. Invest Ophthalmol Vis Sci 1993;34:145–152.

[31] Dong L J, Chung A E. The expression of the genes for entactin, laminin A, laminin B1 and laminin B2 in murine lens morphogenesis and eye development. Differentiation 1991;48:157–172.

[32] Morissette N, Carbonetto S. Laminin α2 chain (M chain) is found within the pathway of avian and murine retinal projections. J Neurosci 1995;15:8067–8082.

[33] Libby R T, Hunter D D, Brunken W J. Developmental expression of laminin β2 in rat retina. Further support for a role in rod morphogenesis. Invest. Ophthalmol Vis Sci 1996;37:1651–1661.

[43] Hunter D D, Shah V, Merlie J P, Sanes J R. A laminin-like adhesive protein concentrated in the synaptic cleft of the neuromuscular junction. Nature 1989;338:229–234.

[44] Noakes P G, Gautam M, Mudd J, Sanes J R, Merlie J P. Aberrant differentiation of neuromuscular junctions in mice lacking s-laminin/laminin β2. Nature 1995;374:258–262.

[45] Libby R T, Yin X, Selfors L M, Brunken W J, Hunter D D. Identification of the cellular source of laminin β2 in adult and developing vertebrate retinae. J Comp Neurol 1997;389:355–367

[46] Sanes J R, Chiu A Y. The basal lamina of the neuromuscular junction. Cold Spring Harb. Symp. Quant Biol 1983;48:667–678.

[47] Sanes J R, Engvall E, Butkowski R, Hunter D D. Molecular heterogeneity of basal laminae: isoforms of laminin and collagen IV at the neuromuscular junction and elsewhere. J Cell Biol 1990a;111:1685–1699.

[48] Rouselle P, Lunstrum G P, Keene D R, Burgeson R E. Kalinin: an epithelium-specific basement membrane adhesion molecule that is a component of anchoring filaments. J Cell Biol 1991;114:567–576.

[49] Sugiyama S, Utani A, Yamada S, Kozak C A, Yamada Y. Cloning and expression of the mouse laminin γ2 (B2t) chain, a subunit of epithelial cell laminin. Eur J Biochem 1995;228:120–128.

[50] Miner J H, Lewis R M, Sanes J R. Molecular cloning of a novel laminin chain, α5, and widespread expression in adult mouse tissues. J Biol Chem 1995;270:28523–28526.

[51] Toti P, De Felice C, Malandrini A, Megha T, Cardone C, Villanova M. Localization of laminin chains in the human retina: possible implications for congenital muscular dystrophy associated with α2-chain of laminin deficiency. Neuromusc Disord 1997;7:21–25.

[52] Utani A, Kopp J B, Kozak C A, Matsuki Y, Amizuka N, Sugiyama S, Yamada Y. Mouse Kalinin B1 (laminin β3 chain): cloning and tissue distribution. Lab Invest 1995;72:300–310.

[53] Sarthy P V, Fu M, Huang J. Subcellular localization of an intermediate filament protein and its MRNA in glial cells. Mol Cell Biol 1989;9:4556–4559.

[54] Kallunki P, Sainio K, Eddy R, Byers M, Kallunki T, Sariola J, Beck K, Jirvonen J, Shows T B, Tryggvason K. A truncated laminin chain homologous to the B2 chain: structure, spatial expression, and chromosomal assignment. J Cell Biol 1992;119:679–693.

[55] Yurchenco P D, Quan Y, Colognato J, Mathus T, Harrison D, Yamada Y, Julian J J. The α chain of laminin-1 is independently secreted and drives secretion of its β- and γ-chain partners. Proc Natl Acad Sci USA 1997;94:10189–10194.

[56] Bunt-Milam A H, Saari J C. Immunocytochemical localization of two retinoid-binding proteins in vertebrate retina. J Cell Biol. 1983;97:703–712.

[57] Libby. R. T., Lavallee, C., Balkema, G. W., Brunken, W. J. and Hunter, D. D. (1998) Characterization of laminin β2 in retinal function. IOVS Supplment 39: S574

[58] Feeney L. The interphotoreceptor space. I. Postnatal ontogeny in mice and rats. Dev Biol 1973;32:101–114.

[59] Rasmussen KE. A morphometric study of the Müller cell cytoplasm in the rat retina. J Ultrastruct Res 1972;39:413–429.

[60]

[61] Erickson P A, Feinstein S C, Lewis G P, Fisher S K. Glial fibrillary acidic protein and its mRNA: ultrastructural detection and determination of changes after CNS injury. J Struct Biol 1992;108:148–161.

[62] Cornbrooks C J, Carey D J, McDonald J A, Timpl R, Bunge R P. In vivo and in vitro observations on laminin production by Schwann cells. Proc Nat. Acad Sci USA 1983;80:3850–3854.

[63] Palm SL, Furcht LT. Production of laminin and fibronectin by Schwannoma cells: cell-protein interactions in vitro and protein localization in peripheral nerve in vivo. J Cell Biol 1983;96:1218–1226.

[64] Chiu A Y, Espinosa de los Monteros A, Cole R A, Loera S, de Vellis J. Laminin and s-laminin are produced and released by astrocytes, Schwann cells, and schwannomas in culture. Glia 1991;4:11–24.

[68] Sanes J R, Hunter D D, Green T L, Merlie J P. S-laminin. Cold Spring Harb Symp Quant Biol 1990b;55:419–430.

[69] Sorokin L M, Pausch F, Frieser M, Kroger S, Ohage E, Deutzmann R. Developmental regulation of the laminin α5 chain suggests a role in epithelial and endothelial cell maturation. Dev Biol 1997;189:285–300.

[70] Xu H, Wu X R, Wewer U M, Engvall E. Murine muscular dystrophy caused by a mutation in the laminin α2 (Lama2) gene. Nat Genet 1994;8:297–302.

[71] Sunada Y, Bernier S M, Utani A, Yamada Y, Campbell K P. Identification of a novel mutant transcript of laminin α2 chain gene responsible for muscular dystrophy and dysmyelination in dy2J mice. Hum Mol Genet 1995;4:1055–1061.

[72] Helbling Leclerc A, Zhang X, Topaloglu H, Cruaud C, Tesson F, Weissenbach J, Tome F M, Schwartz K, Fardeau M, Tryggvason K, Guicheney P. Mutations in the laminin α2-chain gene (LAMA2) cause merosin-deficient congenital muscular dystrophy. Nat Genet 1995;11:216–218.

[73] Liesi P, Dahl D, Vaheri A. Laminin is produced by early rat astrocytes in primary culture. J Cell Biol 1983;96:920–924.

[74] Liesi P, Risteli L. Glial cells of mammalian brain produce a variant form of laminin. Exp Neurol 1989;105:86–92.

[75] Green T L, Hunter D D, Chan W, Merlie J P, Sanes J R. Synthesis and assembly of the synaptic cleft protein s-laminin by cultured cells. J Biol Chem 1992;267:2014–2022.

[76] Liesi P, Hager G, Dodt H U, Seppala I, Zieglgansberger W. Domain-specific antibodies against the B2 chain of laminin inhibit neuronal migration in the neonatal rat cerebellum. J Neurosci Res 1995;40:199–206.

[76] Sanes J R. Extracellular matrix molecules that influence neural development. Ann Rev Neurosci 1989;12:491–516.

Literature Cited Under the Section of "Laminin 5"

Aberdam, D., Aguzzi, A., Baudoin, C., Galliano, M. F., Ortonne, J. P., and Meneguzzi, G. (1994b) Developmental expression of nicein adhesion protein (LAMININ-5) subunits suggests multiple morphogenic roles. *Cell Adhes Commun.* 2:115–129.

Burgeson, R. E., Chiquet, R. D., Ekblom, P., Engla, J., Kleinman, H., Martin, G. R., Meneguzzi, G., Paulsson, M., Sanes, J., Timpl, R., Tyggvason, K., Yamada, Y., and Yurchenco, P. D. (1994) A new nomenclature for the laminins. *Matrix Biol.* 14:209–211.

Carter-Dawson, L. D. and LaVail, M. M. (1979) Rods and cones in the mouse retina. I. Structural analysis using light and electron microscopy. *J Comp Neurol.* 188:245–262.

Cepko, C. L., Austin, C. P., Yang, X., Alexiades, M., and Ezzeddine, D. (1996) Cell fate determination in the vertebrate retina. *Proc Natl Acad Sci USA.* 93:589–595.

Galbavy, E. S. and Olson, M. D. (1979) Morphogenesis of rod cells in the retina of the albino rat: a scanning electron microscopic study. *Anat Rec.* 195:707–717.

Hicks, D. and Barnstable, C. J. (1987) Different rhodopsin monoclonal antibodies reveal different binding patterns on developing and adult rat retina. *J Histochem Cytochem.* 35:1317–1328.

Hinds, J. W. and Hinds, P. L. (1974) Early ganglion cell differentiation in the mouse retina: an electron microscopic analysis utilizing seial sections. *Dev Biol.* 37:381–416.

Hinds, J. W. and Hinds, P. L. (1978) Early development of amacrine cells in the mouser retina: an electron microscopic, serial section analysis. *J Comp Neurol.* 179:277–300.

Hinds, J. W and Hinds, P. L. (1979) Differnetiation of phototreceptors and horizontal cell in the embryonic mouse retina: an electron microscopic, serial section analysis. *J Comp Neurol.* 187:495–511.

Hinds, J. W. and Hinds, P. L. (1983) Development of retinal amacrine cells in the mouse embryo: evidence for two modes of formation. *J Comp Neurol.* 213:1–23.

Hunter, D. D., Murphy, M. D., Olsson, C. V., and Brunken, W. J. (1992a) S-laminin expression in adult and developing retinae: A potential cue for photoreceptor morphogenesis. *Neuron.* 8:399–413.

Hunter, D. D., Llinas, R., Ard, M., Merlie, J. P., and Sanes, J. R. (1992b) Expression of s-laminin and laminin in the developing rat central nervous system. *J Comp Neurol.* 323:238–251.

Libby, R. T., Xu, Y., Selfors, L., Brunken, W. J., and Hunter, D. D. (1997a) Identification of the cellular source of laminin 62 in adult and developing vertebrate retinae. *J Comp Neurol.* 389:655–667.

Libby, R. T., (1997b) Anatomical and functional characterization of laminins in the adult and developing vertebrate retina. Dissertation.

Miner, J. H., Patton, B. L., and Lentz, S. I. (1997) The laminin a chains: Expression, developmental transitions, and chromosomal locations of α1–5, identification of heterotrimeric laminins 8–11, and cloning of a novel α3 isoform. *J Cell Biol.* 137:685–701.

Rousselle, P., Lunstrum, G. P., Keene, D. R., and Burgeson, R. E. (1991) Kalinin: an epithelium-specific basement membrane adhesion molecule that is a component of anchoring filaments. *J Cell Biol.* 114:567–576.

Ryan, M. C., Christiano, A. M., Engvall, E., Wewer, U., Miner, J., Sanes, J., Burgeson, R. (1996) The functions of laminins: Lessons from in vivo studies; The laminins α3 chain. *Matrix Biol.* 15:369–381.

Sanes, J. R. and Chiu, A. Y. (1983) The basal lamina of the neuromuscular junction. *Cold Spring Harb Symp Quant Biol.* 48 Pt 2:667–678.

Sanes, J. R., Engvall, E., Bukowski, R., and Hunter, D. D. (1990) Molecular hetergeneity of basal laminae: isoforms of laminin and collagen IV at the neuromuscular junction and elsewhere. *J Cell Biol* 111:1685–1699.

Sugiyama, S., Utani, A., Yamada, S., Kozak, C. A., and Yamada, Y. (1995) Cloning and expression of the mouse laminin γ2 (B2t) chain, a subunit of epithelial cell laminin. *Eur J Biochem.* 228:120–128.

Weidman, T. A. and Kuwabara, T. (1968) Postnatal development of the rat retina. *Arch Ophthal.* 79:470–484.

Weidman, T. A. and Kuwabara, T. (1969) Development of the rat retina. *Invest Ophthal.* 60–69. Zhao, S., Thornquist, S. C., and Barnstable, C. J. (1995) In vitro transdifferentiation of embryonic rat retinal pigment epithelium to neural retina. *Brain Res.* 677:300–310.

Literatures Cited Under the Section of "Laminin β2-Deficient Mice".

Balkema, G. W. (1991). A synaptic antigen (B16) is localized in retinal synaptic ribbons. J. Comp. Neurol. 312, 573–583.

Balkema, G. W., and Rizkalla, R. (1996). Ultrastructural localization of a synaptic ribbon protein recognized by antibody B16. J. Neurocytol. 25, 565–571.

Barnstable, C. J. (1980). Monoclonal antibodies which recognize different cell types in the rat retina. Nature 286, 231–235.

Brown, K. T., and Wiesel, T. N. (1961). Localization of origins of electroretinogram components by intraretinal recording in the intact cat eye. J. Physiol. 158, 257–280.

Dowling, J. E. (1960). Night blindness, dark adaptation and the electroretinogram. Am. J. Ophthal. 50, 875–889.

Fekete, D. M., and Barnstable, C. J. (1983). The subcellular localization of rat photoreceptor-specific antigens. *J. Neurocytol.* 12:785–803.

Gavrieli, Y., Sherman, Y, and Ben Sasson, S. A. (1992). Identification of programmed cell death in situ via specific labeling of nuclear DNA fragmentation. J. Cell Biol. 119, 493–501.

LaVail, M. M. (1973). Kinetics of rod outer segment renewal in the developing mouse retina. J. Cell Biol. 58, 650–661.

Libby, R. T., D. D. Hunter, and W. J. Brunken (1996) Developmental expression of laminin β2 in rat retina. Further support for a role in rod morphogenesis. Invest. Ophthalmol. Vis. Sci. 37:1651–1661.

Libby, R. T., X. Yin, L. M. Selfors, W. J. Brunken, and D. D. Hunter (1997) Identification of the cellular source of laminin β2 in adult and developing vertebrate retinae. J. Comp. Neurol. 389:355–367

Noakes, P. G., M. Gautam, J. Mudd, J. R. Sanes, and J. P. Merlie (1995a) Aberrant differentiation of neuromuscular juctions in mice lacking s-laminin/laminin β2. Nature 374:258–262.

Stockton, R. A. and Slaughter M. M. (1989). B-wave of the electroretinogram. A reflection of ON bipolar cell activity. J. Gen. Physiol. 93, 101–122.

Vaux, D. L. (1983). Toward an understanding of the molecular mechanisms of physiological cell death. Proc. Natl. Acad. Sci. USA 90, 786–789.

Young, R. W. (1984). Cell death during differentiation of the retina in the mouse. J. Comp. Neurol. 229, 362–373.

What is claimed is:

1. A substantially pure preparation comprising a human laminin wherein the laminin comprises a full length laminin chain α3, a full length laminin chain β2, and a full length laminin chain γ3.

2. A composition comprising the protein preparation of claim 1 and a pharmarcutically acceptable carrier.

3. The preparation of claim 1, wherein the laminin is recombinant.

4. A substantially pure preparation comprising a human laminin wherein the laminin comprises a full length laminin chain α4, a full length laminin chain β2, and a full length laminin chain γ3.

5. A composition comprising the protein preparation of claim 4 and a pharmaceutically acceptable carrier.

6. The preparation of claim 4, wherein the laminin is recombinant.

7. A substantially pure preparation comprising a rat laminin wherein the laminin comprises a full length laminin chain α3, a full length laminin chain β2, and a full length laminin chain γ3.

8. The preparation of claim 7, wherein the laminin is recombinant.

9. A substantially pure preparation comprising a rat laminin wherein the laminin comprises a full length laminin chain α4, a full length laminin chain β2, and a full length laminin chain γ3.

10. The preparation of claim 9, wherein the laminin is recombinant.

* * * * *